US008899493B2

(12) United States Patent
Kim et al.

(10) Patent No.: US 8,899,493 B2
(45) Date of Patent: Dec. 2, 2014

(54) AIR FRESHENER GENERATOR FOR VEHICLE AIR CONDITIONING APPARATUS

(75) Inventors: Jae Ho Kim, Daejeon-si (KR); Yong Jun Jee, Daejeon-si (KR); Eun Gi Min, Daejeon-si (KR); Young Ha Jeon, Daejeon-si (KR); Dong Suk Lee, Daejeon-si (KR); Ki Hong Kim, Daejeon-si (KR); Ji Yong Park, Daejeon-si (KR)

(73) Assignee: Halla Climate Control Corp., Daejeon-si (KR)

( * ) Notice: Subject to any disclaimer, the term of this patent is extended or adjusted under 35 U.S.C. 154(b) by 884 days.

(21) Appl. No.: 13/123,825

(22) PCT Filed: Oct. 14, 2009

(86) PCT No.: PCT/KR2009/005920
§ 371 (c)(1),
(2), (4) Date: Jun. 1, 2011

(87) PCT Pub. No.: WO2010/044611
PCT Pub. Date: Apr. 22, 2010

(65) Prior Publication Data
US 2011/0226866 A1    Sep. 22, 2011

(30) Foreign Application Priority Data

Oct. 14, 2008 (KR) .................. 10-2008-0100846
Jul. 6, 2009 (KR) .................. 10-2009-0061309
Jul. 6, 2009 (KR) .................. 10-2009-0061312
Jul. 6, 2009 (KR) .................. 10-2009-0061323

(51) Int. Cl.
*A61L 9/04* (2006.01)
*A24F 25/00* (2006.01)
*A61L 9/12* (2006.01)
*B60H 3/00* (2006.01)

(52) U.S. Cl.
CPC ............ *A61L 9/12* (2013.01); *B60H 2003/0064* (2013.01); *B60H 3/0021* (2013.01); *B60H 2003/0042* (2013.01); *A61L 9/125* (2013.01)
USPC .................... 239/59; 239/34; 239/58; 239/60

(58) Field of Classification Search
CPC .... A61L 9/12; A01M 1/2055; A01M 1/2083; A01M 1/2077
USPC .................... 239/49, 57, 58, 34, 59; 422/4, 5; 454/75, 157, 337; 222/645, 546, 644
See application file for complete search history.

(56) References Cited

U.S. PATENT DOCUMENTS

| 3,595,417 | A | * | 7/1971 | Musher .......................... 215/222 |
| 4,572,375 | A | * | 2/1986 | Baer .................................. 239/56 |
| 5,180,107 | A | * | 1/1993 | Lindauer ......................... 239/35 |
| 5,297,988 | A |   | 3/1994 | Nishino et al. |
| 5,695,692 | A | * | 12/1997 | Kennedy ........................ 261/30 |
| 5,805,768 | A | * | 9/1998 | Schwartz et al. ............. 392/390 |
| 6,244,518 | B1 | * | 6/2001 | Pogue .............................. 239/36 |
| 8,043,570 | B2 | * | 10/2011 | Feuillard et al. .............. 422/124 |

FOREIGN PATENT DOCUMENTS

| JP | 05-023383 A |   | 2/1993 |
| JP | 2003-237364 A |   | 8/2003 |
| JP | 2004-208896 A |   | 7/2004 |
| KR | 10-0473446 | * | 10/2003 |
| KR | 10-0473446 B1 |   | 3/2005 |
| KR | 10-2006-0014429 A |   | 2/2006 |

* cited by examiner

*Primary Examiner* — Len Tran
*Assistant Examiner* — Alexander M Valvis
(74) *Attorney, Agent, or Firm* — Jefferson IP Law, LLP

(57) ABSTRACT

An air freshener generating apparatus of a vehicle air conditioning system includes a body in which an inlet pipe is communicated with an outlet pipe and on a circumferential surface of which ball plungers are mounted at intervals along circumferential lines on which the inlet pipe and the outlet pipe are located respectively, a cartridge rotatably coupled to the body and having at least one partition wall such that at least one air freshener emitter is filled within spaces defined by the partition wall, the cartridge having through-holes facing the ball plungers, and an actuator configured to rotate the cartridge by a predetermined angle. When the cartridge is rotated by the predetermined angle, air is supplied through the through-hole facing the inlet pipe such that one air freshener is discharged through the through-hole facing the outlet pipe, and the ball plungers are configured to block the rest of the through-holes.

17 Claims, 26 Drawing Sheets

AIR FRESHENER GENERATOR FOR VEHICLE AIR CONDITIONING APPARATUS

TECHNICAL FIELD

The present invention relates to an air freshener generating apparatus of a vehicle air conditioning system, and more particularly, to an air freshener generating apparatus of a vehicle air conditioning system which is adapted to selectively send different sorts of air fresheners filled in a cartridge into an interior of a vehicle.

BACKGROUND ART

In general, a vehicle air conditioning system is adapted to cool or heat an interior of a vehicle by selectively passing exterior air introduced into the interior of the vehicle through an evaporator unit through which a refrigerant flows or a heater core unit through which cooling water of an engine flows to exchange heat, and distributing cold air or hot air to various directions of the interior of the vehicle through a defrost vent, a face vent, and a floor vent communicated with respective portions of the interior of the vehicle.

When a heater or an air conditioner is operated during travelling of a vehicle, various harmful substances such as dust on a road or exhaust gases are introduced into an interior of the vehicle. Especially when a vehicle air conditioning system is operated on a wet day, since bacterial substances such as fungi living in an air conditioning duct are introduced into an interior of a vehicle as they are, an air freshener generating apparatus for purifying air in the interior of the vehicle is mounted on the vehicle.

A conventional air freshener generating apparatus is disclosed in Japanese Patent Application Publication No. 2003-237364 (hereinafter, Patent Document 1). As illustrated in FIG. 1, the air freshener generating apparatus 10 of Patent Document 1 is attached to a corner 14 of a glove box 12 by means of a support plate 20. As illustrated in FIG. 2, the air freshener generating apparatus 10 includes a body 68, a cartridge 78, an adjusting member 56, a packing 44, a support plate 20, an actuator 24, etc.

However, in the air freshener generating apparatus 10 of Patent Document 1, since the cartridge 78 is configured to be rotated by the actuator 24 with the packing 44 and the adjusting member 56 being in contact with each other between the cartridge 78 and a seat 32 of the support plate 20, an air freshener may be leaked as the packing 44 and the adjusting member 56 are worn due to their contact.

Meanwhile, since a rectangular opening 34 is formed in the seat 32 of the support plate 20 and a square opening 58 is formed in the adjusting member 56 such that an air freshener is leaked when the cartridge 78 rotates and moves, different types of air fresheners may be introduced into an interior of the vehicle.

As illustrated in FIG. 3, U.S. Pat. No. 5,297,988 (hereinafter, Patent Document 2) discloses an air freshener generating apparatus 1 in which an inlet pipe 31 is formed on the front side of an evaporator 23 and an outlet pipe 32 is formed on a side of a duct and which is configured to intermittently control air fresheners with a plurality of control valves 12A to 12D.

However, since the air freshener generating apparatus 1 of Patent Document 2 needs a plurality of control valves 12A to 12D, a valve control circuit 13, and selection switches 14A, 14B, and 14C to intermittently control different air fresheners, a mechanism required to discharge the air fresheners is complex.

DISCLOSURE

Technical Problem

Therefore, the present invention has been made in view of the above-mentioned problems of the air freshener generating apparatuses of Patent Documents 1 and 2, and the present invention provides an air freshener (aroma, perfume etc.) generating apparatus for a vehicle which is adapted to introduce a selected air freshener into an interior of the vehicle without leaking the air freshener and simplify a mechanism for discharging an air freshener from a cartridge.

Technical Solution

In accordance with an aspect of the present invention, there is provided an air freshener generating apparatus of a vehicle air conditioning system including: a body in which an inlet pipe is communicated with an outlet pipe and on a circumferential surface of which ball plungers are mounted at intervals along circumferential lines on which the inlet pipe and the outlet pipe are located respectively; a cartridge coupled to the body and having at least one partition wall such that at least one air freshener emitter is filled within spaces defined by the partition wall, the cartridge having through-holes; and an actuator configured to rotate the cartridge by a predetermined angle, wherein, when the cartridge is rotated by the predetermined angle, air is supplied through the through-hole facing the inlet pipe such that one air freshener is discharged through the through-hole facing the outlet pipe.

The cartridge may be mounted on an inner circumferential surface of the body and a resilient force of the ball plunger is applied on an outer circumferential surface of the cartridge toward the center of the cartridge. The cartridge may be mounted on an outer circumferential surface of the body and a resilient force of the ball plunger may be applied on an inner circumferential surface of the cartridge.

Preferably, the air freshener generating apparatus may further include a positioning unit including magnets mounted on portions of the body where a communication with the inlet pipe and with the outlet pipe are accomplished, and metal members mounted on peripheries of the through-holes of the cartridge. In the positioning unit, metal members may be formed in the body and magnets may be formed at the peripheries of the through-holes of the cartridge.

Preferably, grooves by which the ball plungers are guided may be formed in a plurality of rows on the outer or inner circumferential surface of the cartridge.

Preferably, whenever the cartridge is rotated clockwise or counterclockwise with respect to the body 90 degrees, different air fresheners may be selected and discharged.

Preferably, the cartridge may have flexible contact members on inner and peripheral portions of the through-holes so that the ball plungers contact and push the flexible contact members to prevent air fresheners from being leaked.

Preferably, inclined surfaces having a certain angle may be formed at upper portions of the through-holes so that the ball plungers come into surface-contact with the flexible contact members.

Preferably, a plurality of wrinkled portions may be formed in the flexible contact members on the inclined surface at certain intervals.

A baffle configured to block a passage formed by the partition wall and to let the air fresheners pass through lower portion thereof is mounted on the cartridge, the air freshener emitters being supported by the baffle, and flow passages being formed along a periphery of the partition wall.

The baffle includes a plate having a plurality of through-holes within a certain width at a lower circumference thereof and a support extending to opposite sides from the plate to support the air freshener emitters.

In accordance with another aspect of the present invention, there is provided an air freshener generating apparatus for a vehicle including: a body in which an inlet pipe and an outlet pipe are formed to be communicated with each other and to which ball plungers are mounted along a circumferential surface thereof at a predetermined interval; a cartridge mounted within the body and filled with at least one air freshener emitter; and an actuator configured to rotate by the cartridge a predetermined angle, wherein the cartridge includes a holding plate having a coupling portion at one side thereof, and at least one sub-cartridges independently coupled to the coupling portion of the holding plate and having through-holes respectively.

A guide rod is formed along the center line of the holding plate and cutaway portions are formed on upper and lower sides of the guide rod, wherein each sub-cartridge has a guide recess and a boss corresponding to the guide rod and the cutaway portion, and wherein the guide rod is coupled to the guide recesses and the bosses are coupled to the cutaway portions respectively.

Two sub-cartridges are provided and the air freshener emitter is filled in one of the two sub-cartridges.

Advantageous Effects

According to the air freshener generating apparatus of a vehicle air conditioning system of the present invention, whenever a cartridge rotates clockwise or counterclockwise by a predetermined angle (90 degrees) with respect to the body, air is supplied through a through-hole facing an inlet pipe and a selected air freshener is discharged through a through-hole facing an outlet pipe. Meanwhile, through-holes which do not face the inlet pipe and the outlet pipe are blocked by ball plungers. Accordingly, a mechanism for discharging an air freshener from the cartridge can be simplified. Therefore, an air freshener can be prevented from being mixed with another air freshener when it is discharged, and the in-use time of air fresheners can be prolonged.

BRIEF DESCRIPTION OF THE DRAWINGS

The foregoing and other objects, features and advantages of the present invention will become more apparent from the following detailed description when taken in conjunction with the accompanying drawings in which.

BEST MODE

Mode for Invention

Embodiment 1

Figure 1:
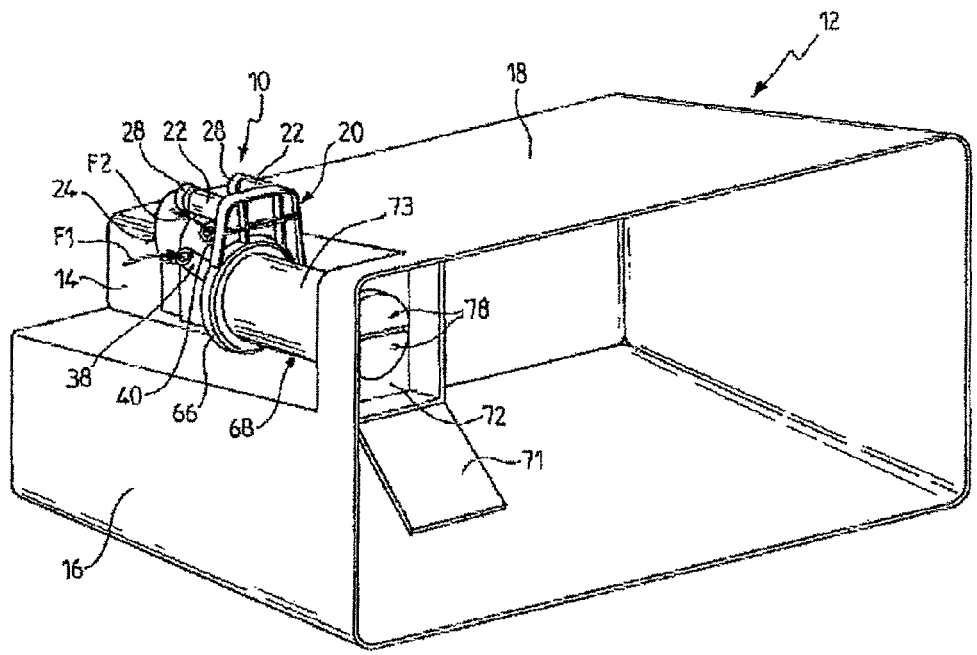
FIG. 1 is a view illustrating a conventional air freshener generating apparatus installed in a glove box.
Figure 2:
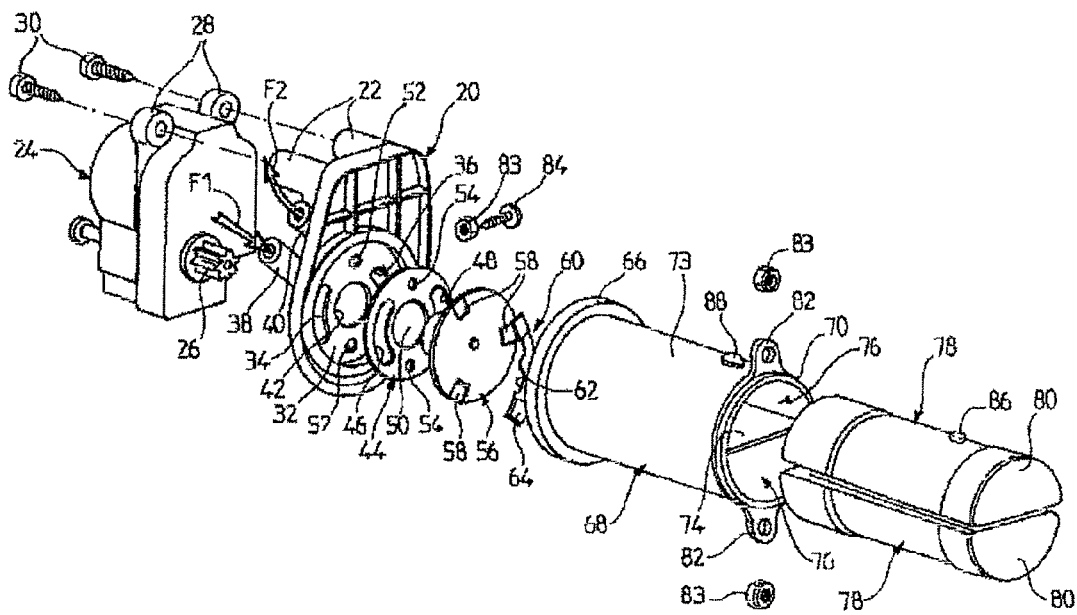
FIG. 2 is an exploded perspective view of the air freshener generating apparatus of FIG. 1.
Figure 3:
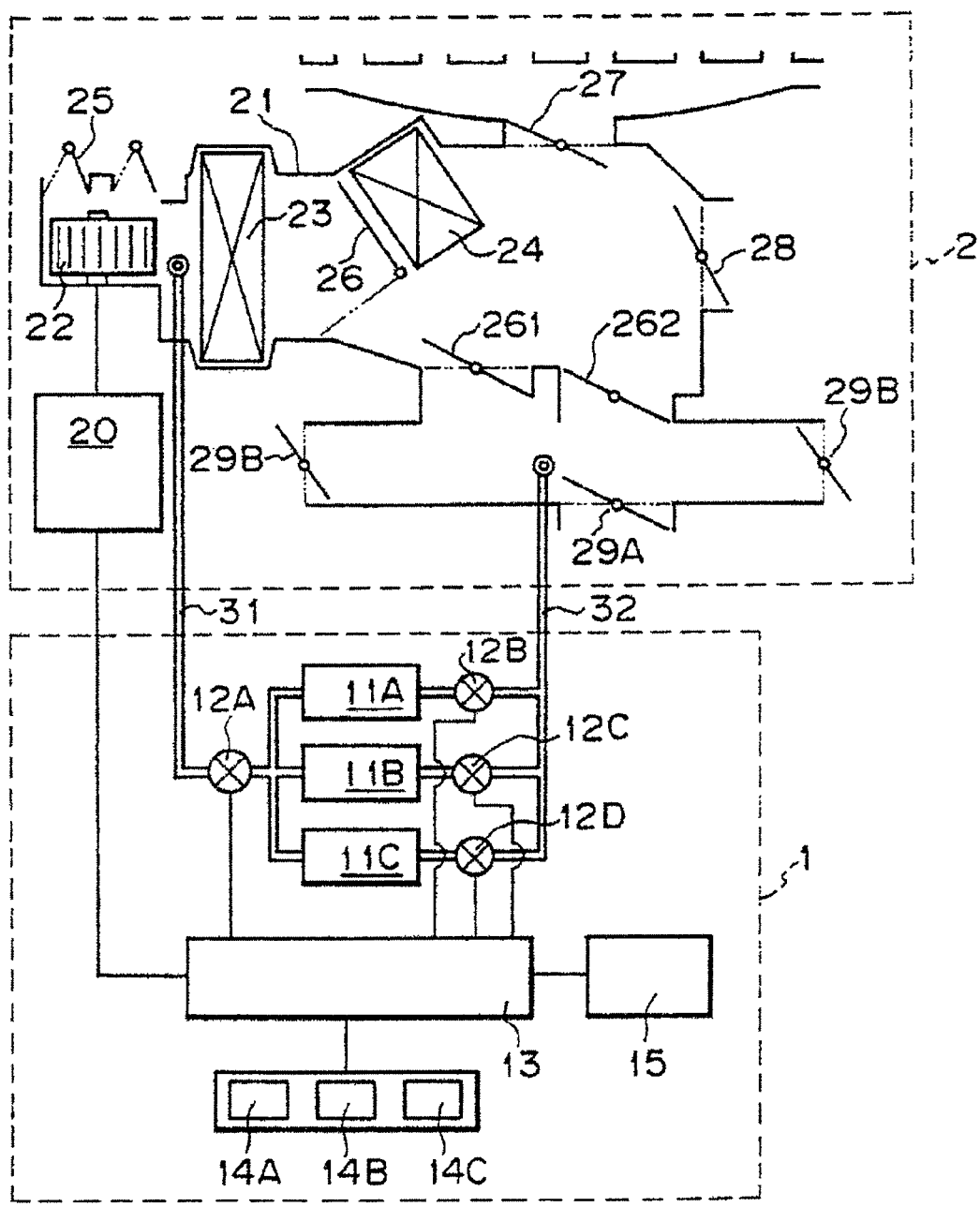
FIG. 3 is a diagram illustrating another conventional air freshener generating apparatus.
Figure 4:
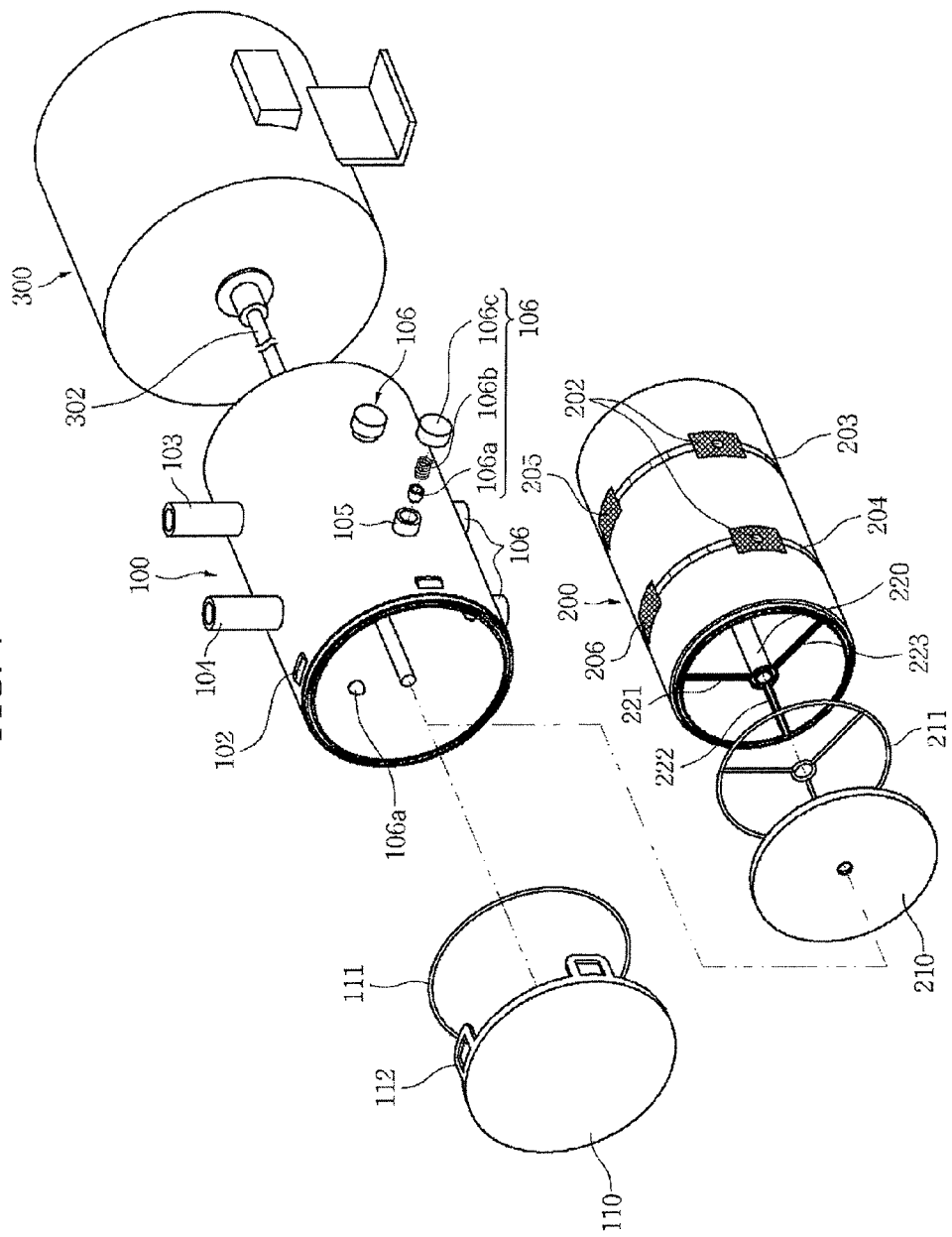
FIG. 4 is an exploded perspective view illustrating an air freshener generating apparatus according to the first embodiment of the present invention.
Figure 5:
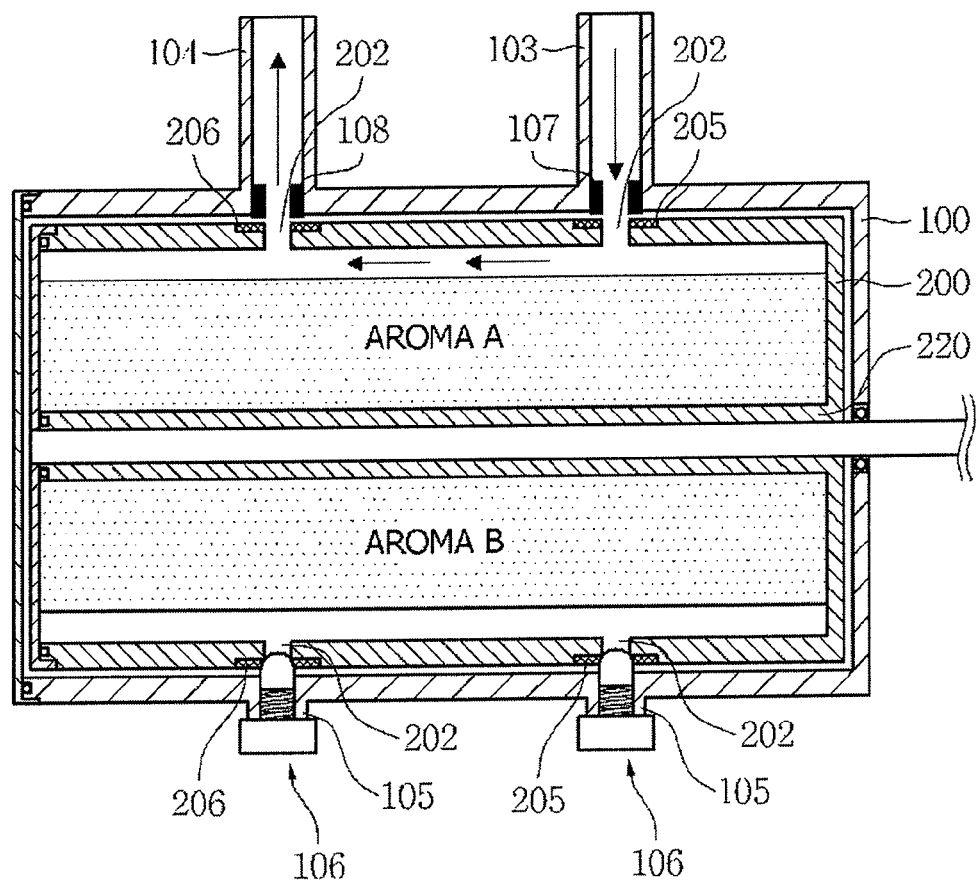
FIGS. 5 and 6 are a transverse sectional view and a longitudinal sectional view of the air freshener generating apparatus according to the first embodiment of the present invention, respectively.
Figure 6:
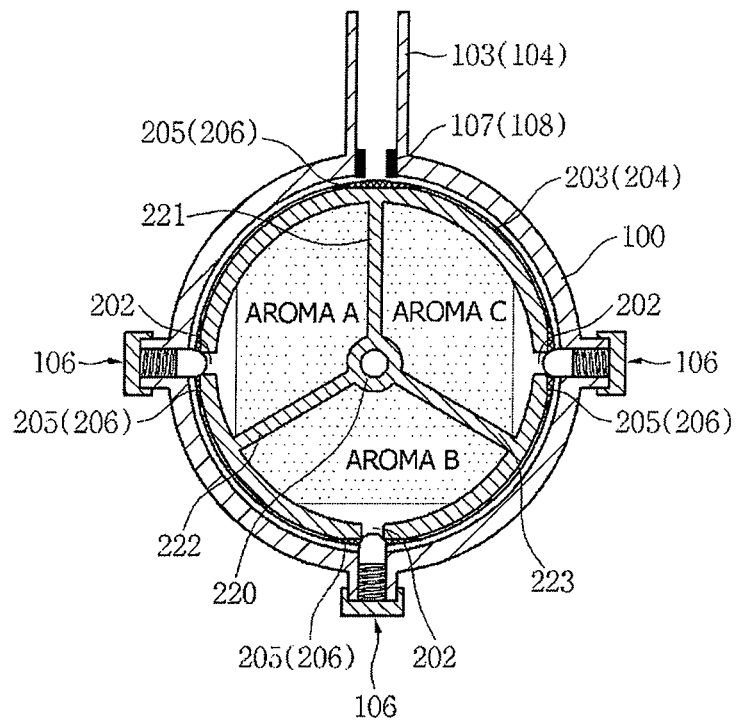

FIG. 4 is an exploded perspective view illustrating an air freshener generating apparatus according to the first embodiment of the present invention. FIGS. 5 and 6 are a transverse sectional view and a longitudinal sectional view of the air freshener generating apparatus according to the first embodiment of the present invention, respectively.

As illustrated in FIG. 4, the air freshener generating apparatus according to the first embodiment of the present invention includes a body 100, a cartridge 200 mounted within the body 100, and an actuator 300 configured to drive the cartridge 200. Here, although not illustrated in the figure, the body 100 and the cartridge 200 are covered by a casing.

The body 100 has a cylindrical shape and a cap 110 is coupled with the body 100. Here, a sealing O-ring 111 is interposed between the body 100 and the cap 110. A plurality of coupling portions 112 extend from a tip end of the cap 110 to be coupled to coupling bosses 102 formed at a tip end of the body 100.

An inlet pipe 103 and an outlet pipe 104 radially protrude from a circumferential surface of the body 100 such that they are spaced apart from each other along a lengthwise direction of the body 100 and are communicated with each other.

As illustrated in FIGS. 4 and 5, a plurality of through-holes 105 are formed on the circumferential surface of the body 100 such that they are spaced apart from the inlet pipe 103 and the outlet pipe 104 at certain angles, and ball plungers 106 are mounted on the through-holes 105 respectively.

Each ball plunger 106 includes a ball 106a, a spring 106b for providing resiliency to the ball 106a, and a support member 106c supporting the spring 106b. Here, a total of six ball plungers 106 are mounted on the circumferential surface of the body 100 such that three of them are mounted along the same circumferential line as the inlet pipe 103 and the remaining ball plungers 106 are mounted along the same circumferential line as the outlet pipe 104. The inlet pipe 103 and the three plungers 106 are disposed at intervals of 90 degrees along the circumferential surface of the body 100. Likewise, the outlet pipe 104 and the three ball plungers 106 are disposed at intervals of 90 degrees along the circumferential surface of the body 100.

As illustrated in FIGS. 4 and 5, the support members 106a of the ball plungers 106 are coupled to the through-holes 105 such that the balls 106a apply resilient forces toward the center of the cartridge 200 on the outer peripheral surface of the cartridge 200.

Meanwhile, as illustrated in FIGS. 5 and 6, magnets 107 and 108 are mounted on portions of the body 100 where a communication with the inlet pipe 103 and with the outlet pipe 104 are accomplished.

As illustrated in FIG. 4, the cartridge 200 has a cylindrical shape and is mounted within the body 100. A cap 210 is coupled with the cartridge 200. A sealing O-ring 211 is interposed between the cartridge 200 and the cap 210.

As illustrated in FIGS. 4 and 6, a boss 220 is formed at a central portion of the cartridge 200, and three partition walls 221, 222, and 223 are formed with respect to the boss 220 such that different air freshener emitters (air freshener A emitter, air freshener B emitter, and air freshener C emitter) can be filled in the cartridge 200.

The cartridge 200 has through-holes 202 at portions facing the ball plungers 106, and grooves 203 and 204 through which the ball plungers 106 are guided are formed on the outer circumferential surface of the cartridge 200. Here, the groove 203 is formed along a circumferential direction of the cartridge 200 to correspond to the inlet pipe 103. The groove 204 is formed along a circumferential direction of the cartridge 200 to correspond to the outlet pipe 104.

As illustrated in FIGS. 4 and 5, metal members 205 and 206 are mounted around the through-holes 202 respectively. Here, with reference to FIG. 4, metal members 205 and 206 are also formed on the circumferential surface of the cartridge 200 at portions where the through-holes 202 are not formed.

The magnets 107 and 108 and the metal members 205 and 206 constitute a positioning unit for accurately determining an angular position of the cartridge 200 with respect to the body 100.

As illustrated in FIG. 4, a rotary shaft 302 of the actuator 300 is inserted into the boss 220 of the cartridge 200 so that the cartridge 200 can be rotated clockwise or counterclockwise.

The actuator 300 is adapted to rotate the cartridge 200 clockwise or counterclockwise by 90 degrees.

Hereinafter, an air freshener discharging operation of the air freshener generating apparatus according to the first embodiment of the present invention will be described with reference to FIGS. 5 to 9.

As illustrated in FIG. 6, if a portion of the cartridge 200 where the through-holes 202 are not formed is located at the inlet pipe 103 of the body 100, air is prevented from being introduced into the cartridge 200. Then, since the ball plungers 106 block all the through-holes 202 of the cartridge 200, all the air fresheners (an air freshener A, an air freshener B, and an air freshener C) are prevented from being discharged.

If the cartridge 200 is rotated clockwise by 90 degrees from the state of FIG. 6, air is introduced into the through-hole 202 through the inlet pipe 103 and the air freshener A is discharged through the outlet pipe 104. Here, when the cartridge 200 is rotated clockwise, the ball plungers 106 are guided by the grooves 203 and 204. When the pair of through-holes 202 approach the inlet pipe 103 and the outlet pipe 204, they are accurately positioned by the positioning unit, i.e. the magnets 107 and 108 and the metal members 205 and 206.

Figure 7:
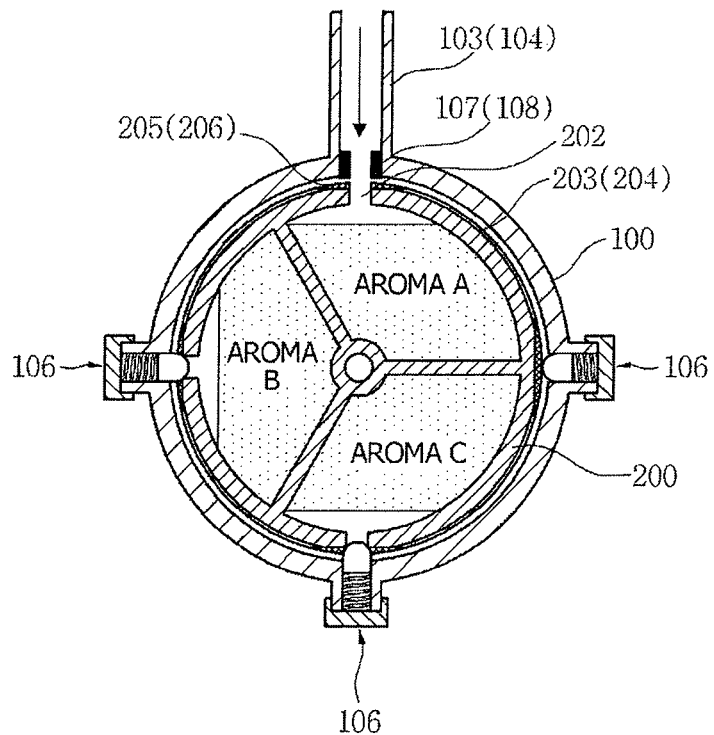
FIGS. 7 to 9 are views illustrating an operation of discharging air fresheners in the air freshener generating apparatus according to the first embodiment of the present invention.
Figure 8:
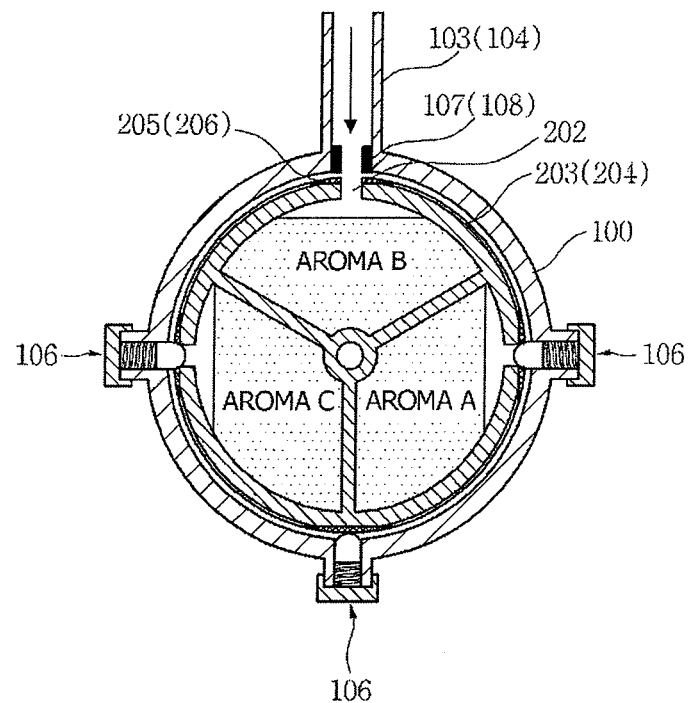

Thereafter, if the cartridge 200 is rotated clockwise by 90 degrees from the state of FIG. 7, air is introduced into the through-hole 202 through the inlet pipe 103 and the air freshener B is discharged through the outlet pipe 104 as illustrated in FIG. 8.

Figure 9:
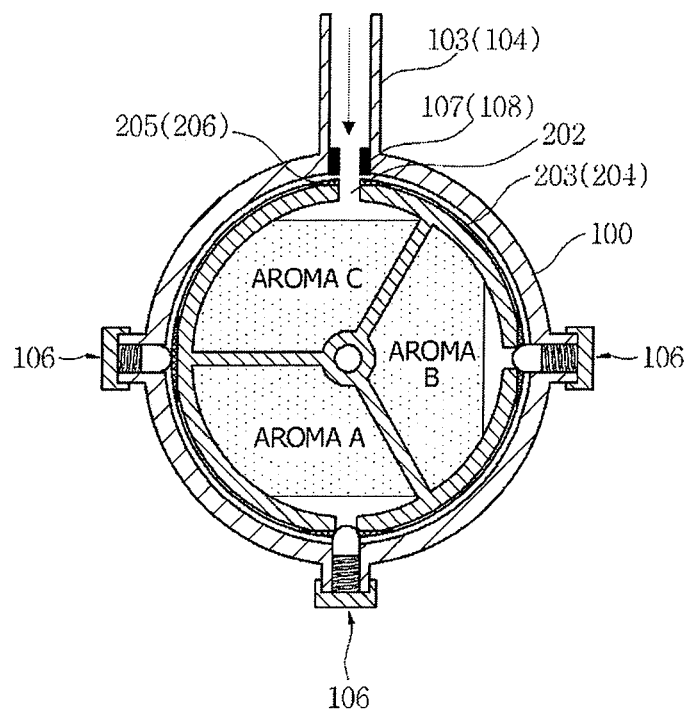

Thereafter, if the cartridge 200 is rotated clockwise by 90 degrees from the state of FIG. 8, air is introduced into the through-hole 202 through the inlet pipe 103 and the air freshener C is discharged through the outlet pipe 104 as illustrated in FIG. 9.

If the cartridge 200 is rotated clockwise by 90 degrees from the state of FIG. 9, air is prevented from being introduced into the cartridge 200 such that none of the air fresheners (the air freshener A, the air freshener B, and the air freshener C) is discharged.

Meanwhile, when the cartridge 20 is sequentially rotated counterclockwise 90 degrees from the state of FIG. 6, the air freshener C, the air freshener B, and the air freshener A are sequentially discharged.

According to the air freshener generating apparatus according to the first embodiment of the present invention, the cartridge 200 is mounted on inner circumferential surface of the body 100 such that only an air freshener is selected and discharged through a pair of through-holes 202 facing the inlet pipe 103 and the outlet pipe 104 whenever the cartridge 200 is rotated clockwise or counterclockwise 90 degrees by the actuator 300. Then, since the other through-holes 202 are blocked by the ball plungers 106, the selected air freshener is prevented from being mixed with the other air fresheners when it is discharged.

Embodiment 2

Figure 10:
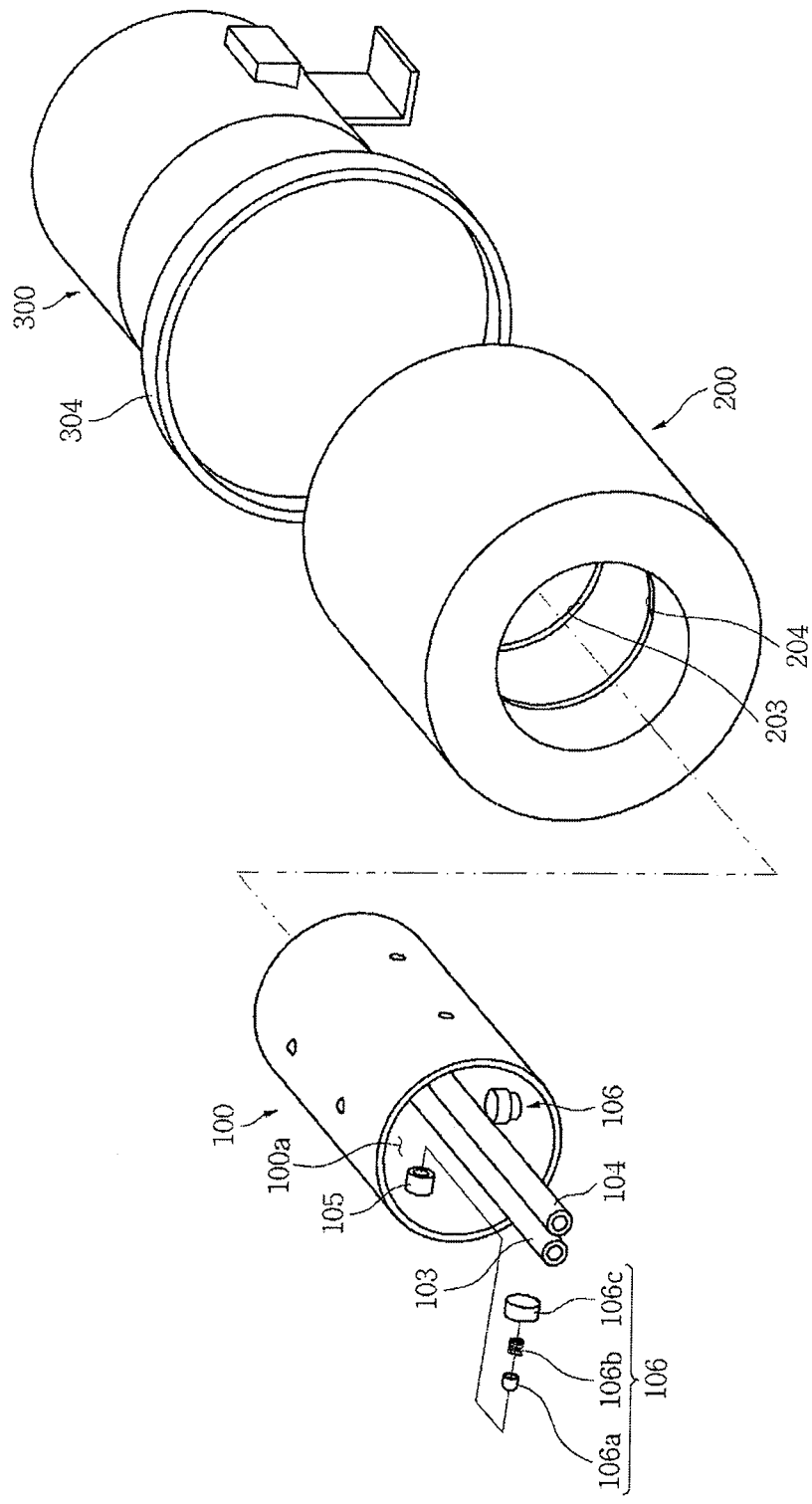
FIG. 10 is an exploded perspective view illustrating an air freshener generating apparatus according to the second embodiment of the present invention.
Figure 11:
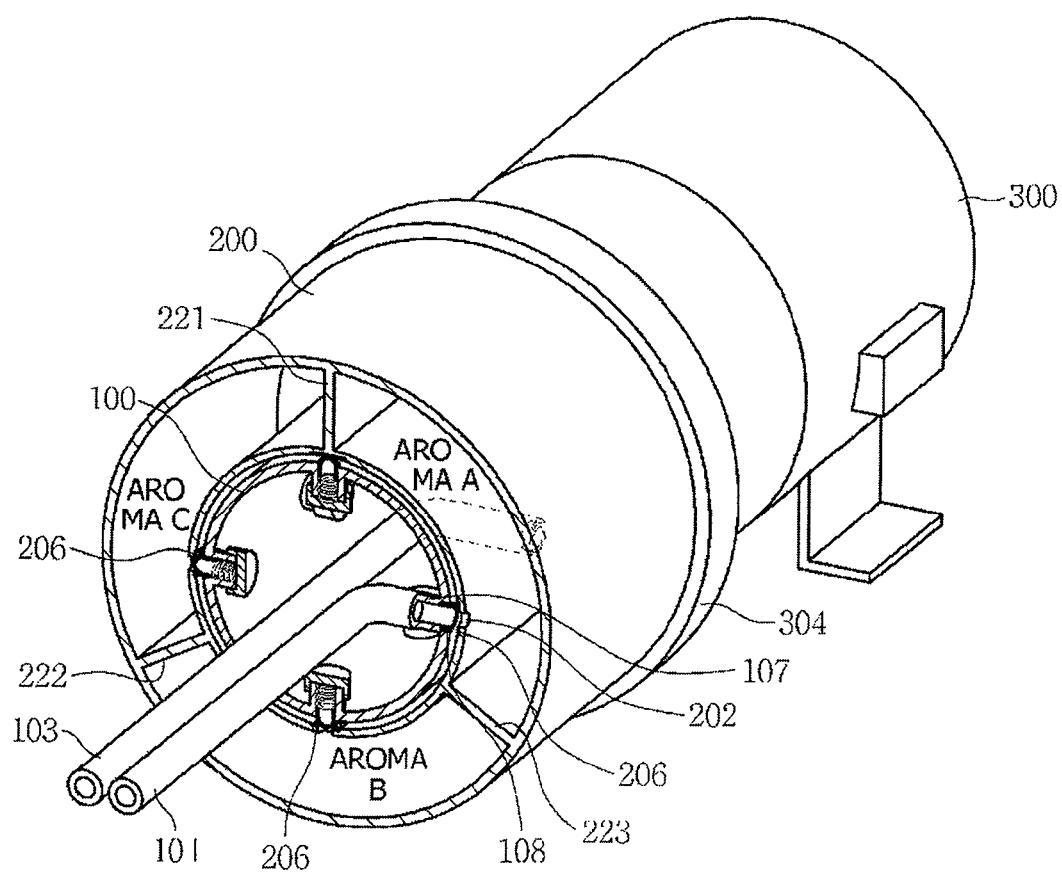
FIG. 11 is a partial sectional perspective view illustrating the air freshener generating apparatus according to the second embodiment of the present invention.

FIG. 10 is an exploded perspective view illustrating an air freshener generating apparatus according to the second embodiment of the present invention. FIG. 11 is a partial sectional perspective view illustrating the air freshener generating apparatus according to the second embodiment of the present invention.

As illustrated in FIG. 10, the air freshener generating apparatus according to the second embodiment of the present invention includes a body 100, a cartridge 200 mounted on the body 100, and an actuator 300 configured to drive the cartridge 200. Here, the cartridge 200 is mounted on an outer circumferential surface of the body 100.

The body 100 has a cylindrical shape having a hollow portion 100a such that an inlet pipe 103 and an outlet pipe 104 are arranged in parallel within the hollow portion 100a of the body 100 and are in communication with an inside of the body 100.

Through-holes 105 are formed on an inner circumferential surface of the body to be spaced apart from the inlet pipe 103 and the outlet pipe 104 at certain angles, respectively, and ball plungers 106 are mounted on the through-members 105, respectively.

Each ball plunger 106 includes a ball 106a, a spring 106b for providing resiliency to the ball 106a, and a support member 106c for supporting the spring 106b. Here, a total of six ball plungers 106 are mounted on the inner circumferential surface of the body 100 such that three of them are mounted along the same circumferential line as the inlet pipe 103 and the remaining ball plungers 106 are mounted along the same circumferential line as the outlet pipe 104. Here, the inlet pipe 103 and the outlet pipe 104 mounted on the body 100 and the three plungers 106 are disposed at intervals of 90 degrees.

As illustrated in FIG. 10, the support members 106a of the ball plungers 106 are coupled to the through-holes 105 such that the balls 106a apply resilient forces on the inner circumferential surface of the cartridge 200.

Figure 12:
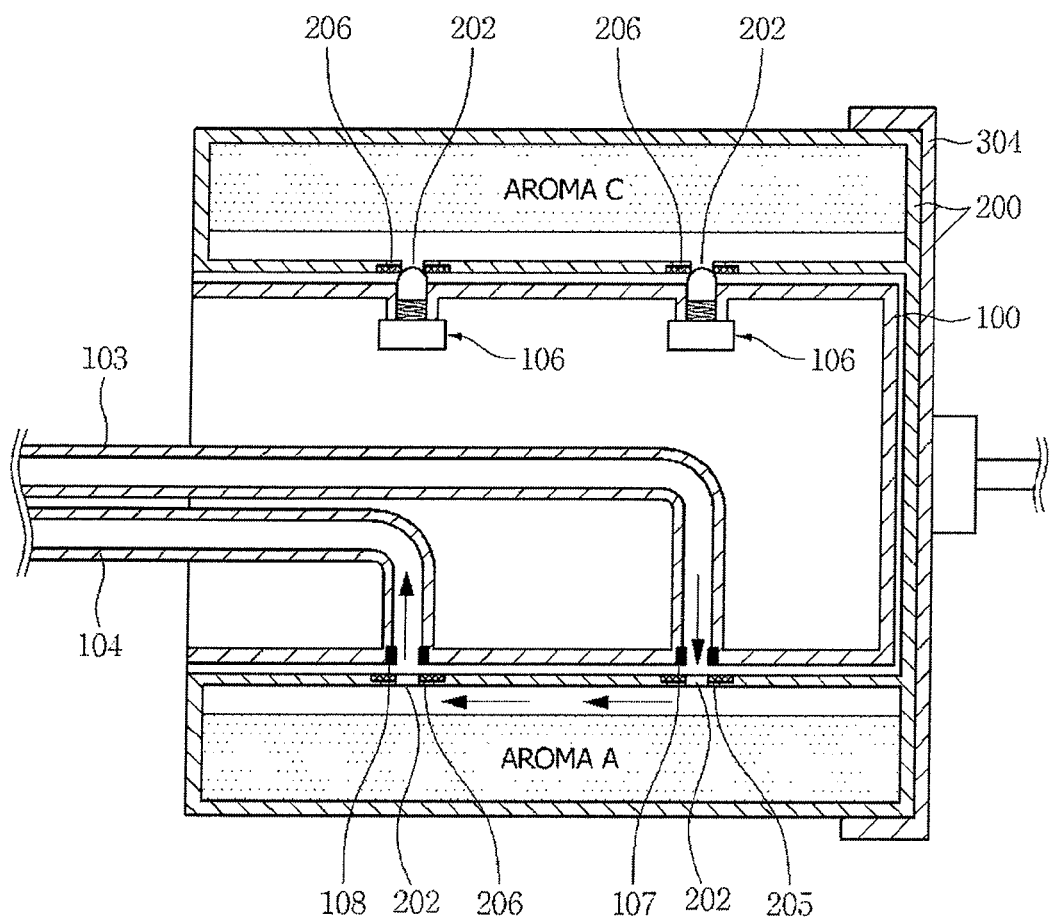
FIG. 12 is a transverse sectional view illustrating the air freshener generating apparatus according to the second embodiment of the present invention.

As illustrated in FIGS. 11 and 12, magnets 107 and 108 are mounted on portions of the body 100 where a communication with the inlet pipe 103 and with the outlet pipe 104 are accomplished.

As illustrated in FIGS. 10 and 11, the cartridge 200 has a hollow cylindrical shape and the body 100 is inserted into the cartridge 200.

As illustrated in FIG. 11, three partition walls 221, 222, and 223 are formed within the cartridge 200 such that different air freshener emitters (an air freshener A emitter, an air freshener B emitter, and an air freshener C emitter) can be filled in the cartridge 200, and through-holes 200 are formed on an inner surface of the cartridge 200 at locations facing the ball plungers 106. As illustrated in FIG. 10, grooves 203 and 204 by which the ball plungers 106 are guided are formed on the inner circumferential surface of the cartridge 200, respectively.

Here, the groove 203 is formed along a circumferential direction of the cartridge 200 to correspond to the inlet pipe 103, and the groove 204 is formed along a circumferential direction of the cartridge 200 to correspond to the outlet pipe 104.

Meanwhile, as illustrated in FIG. 12, metal members 205 and 206 are mounted around the through-holes, respectively. The magnets 107 and 108 and the metal members 205 and 206 constitute a positioning unit for accurately determining an angular position of the cartridge 200 with respect to the body 100.

As illustrated in FIG. 10, a cartridge fixing member 304 is mounted on an axial tip end of the actuator 300 so that the actuator 300 can fix an end of the cartridge 200.

The actuator 300 is adapted to rotate the cartridge 200 clockwise or counterclockwise by 90 degrees.

Hereinafter, an air freshener discharging operation of the air freshener generating apparatus according to the second embodiment of the present invention will be described with reference to FIGS. 12 to 16.

Figure 13:
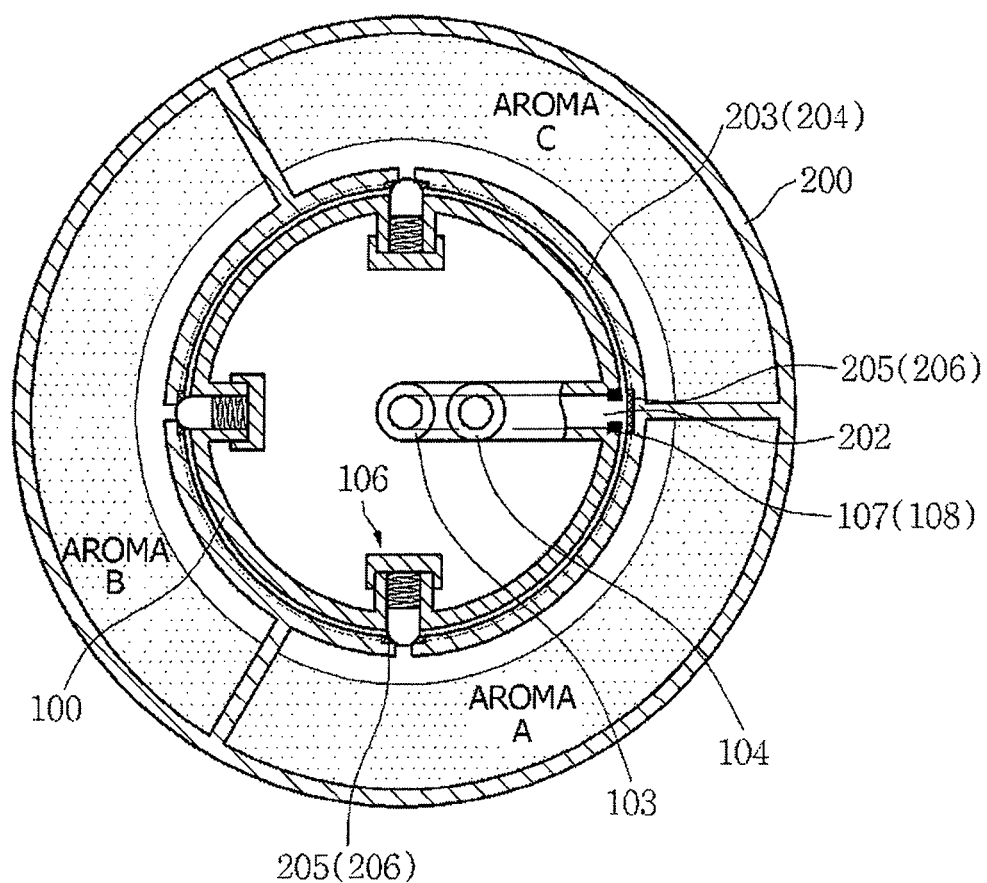
FIGS. 13 to 16 are views illustrating an operation of discharging air fresheners in the air freshener generating apparatus according to the second embodiment of the present invention.

As illustrated in FIG. 13, if portions of the cartridge 200 where the through-holes 202 are not formed are located at the inlet pipe 103 and the outlet pipe 104 of the body 100, air is prevented from being introduced into the cartridge 200. Then, since the ball plungers 106 block all the through-holes 202 of the cartridge 200, all the air fresheners (the air freshener A, the air freshener B, and the air freshener C) are prevented from being discharged.

Figure 14:
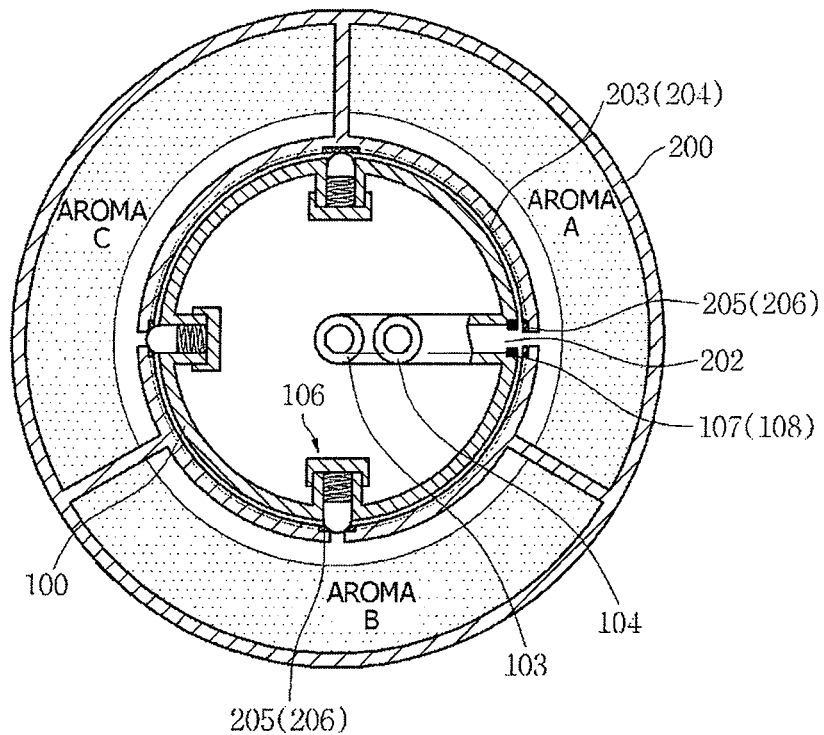

If the cartridge 200 is rotated counterclockwise by 90 degrees from the state of FIG. 13, air is introduced into the through-hole 202 through the inlet pipe 103 and the air freshener A is discharged through the outlet pipe 104 as illustrated in FIGS. 12 and 14.

Figure 15:
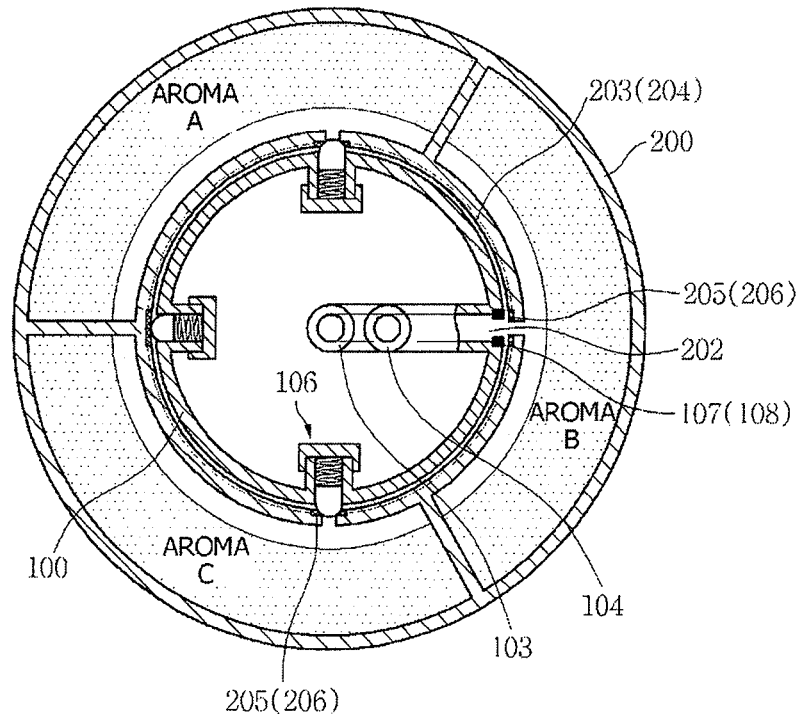

Thereafter, if the cartridge 200 is rotated counterclockwise by 90 degrees from the state of FIG. 14, air is introduced into the through-hole 202 through the inlet pipe 103 and the air freshener B is discharged through the outlet pipe 104 as illustrated in FIG. 15.

Figure 16:
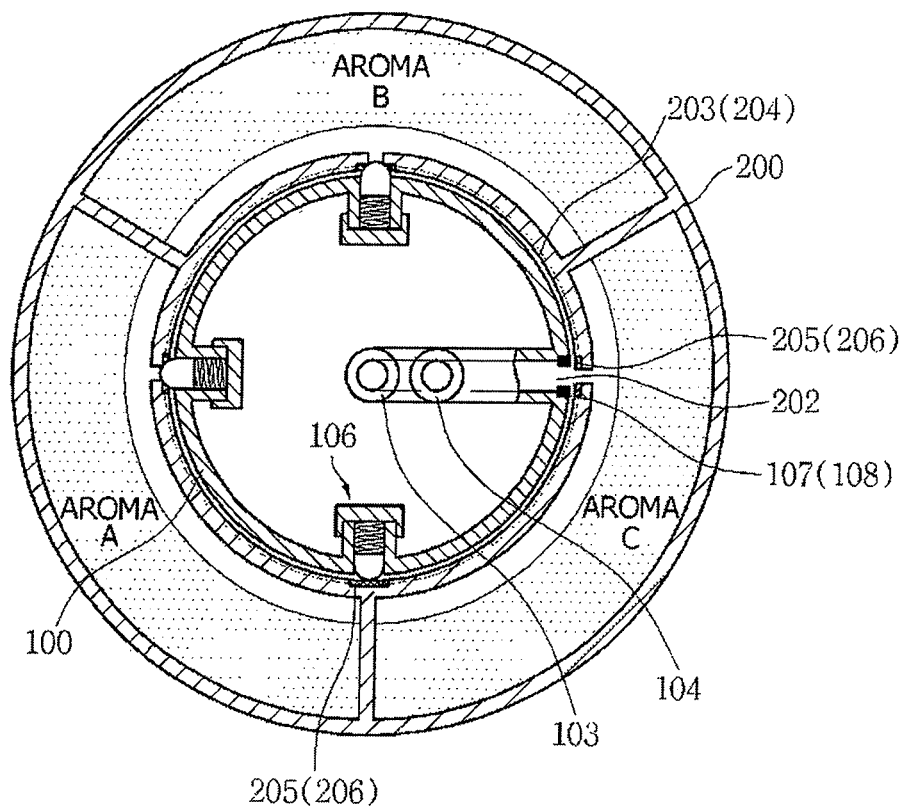

Thereafter, if the cartridge 200 is rotated counterclockwise by 90 degrees from the state of FIG. 15, air is introduced into the through-hole 202 through the inlet pipe 103 and the air freshener C is discharged through the outlet pipe 104 as illustrated in FIG. 16.

When the cartridge 200 is rotated counterclockwise, the ball plungers 106 are guided by the grooves 203 and 204. When the pair of through-holes 202 approach the inlet pipe 103 and the outlet pipe 204, they are accurately positioned by the positioning unit, i.e. the magnets 107 and 108 and the metal members 205 and 206 as illustrated in FIGS. 13 to 15.

If the cartridge 200 is rotated counterclockwise by 90 degrees from the state of FIG. 16, it returns to the original state of FIG. 13 and air is prevented from being introduced into the cartridge 200 such that none of the air fresheners (the air freshener A, the air freshener B, and the air freshener C) is discharged.

Meanwhile, when the cartridge 20 is sequentially rotated clockwise 90 degrees from the state of FIG. 13, the air freshener C, the air freshener B, and the air freshener C are sequentially discharged.

According to the air freshener generating apparatus according to the second embodiment of the present invention, the cartridge 200 is mounted on the outer circumferential surface of the body 100 such that only an air freshener is selected and discharged through a pair of through-holes 202 facing the inlet pipe 103 and the outlet pipe 104 whenever the cartridge 200 is rotated counterclockwise or clockwise 90 degrees by the actuator 300.

Embodiment 3

Figure 17:
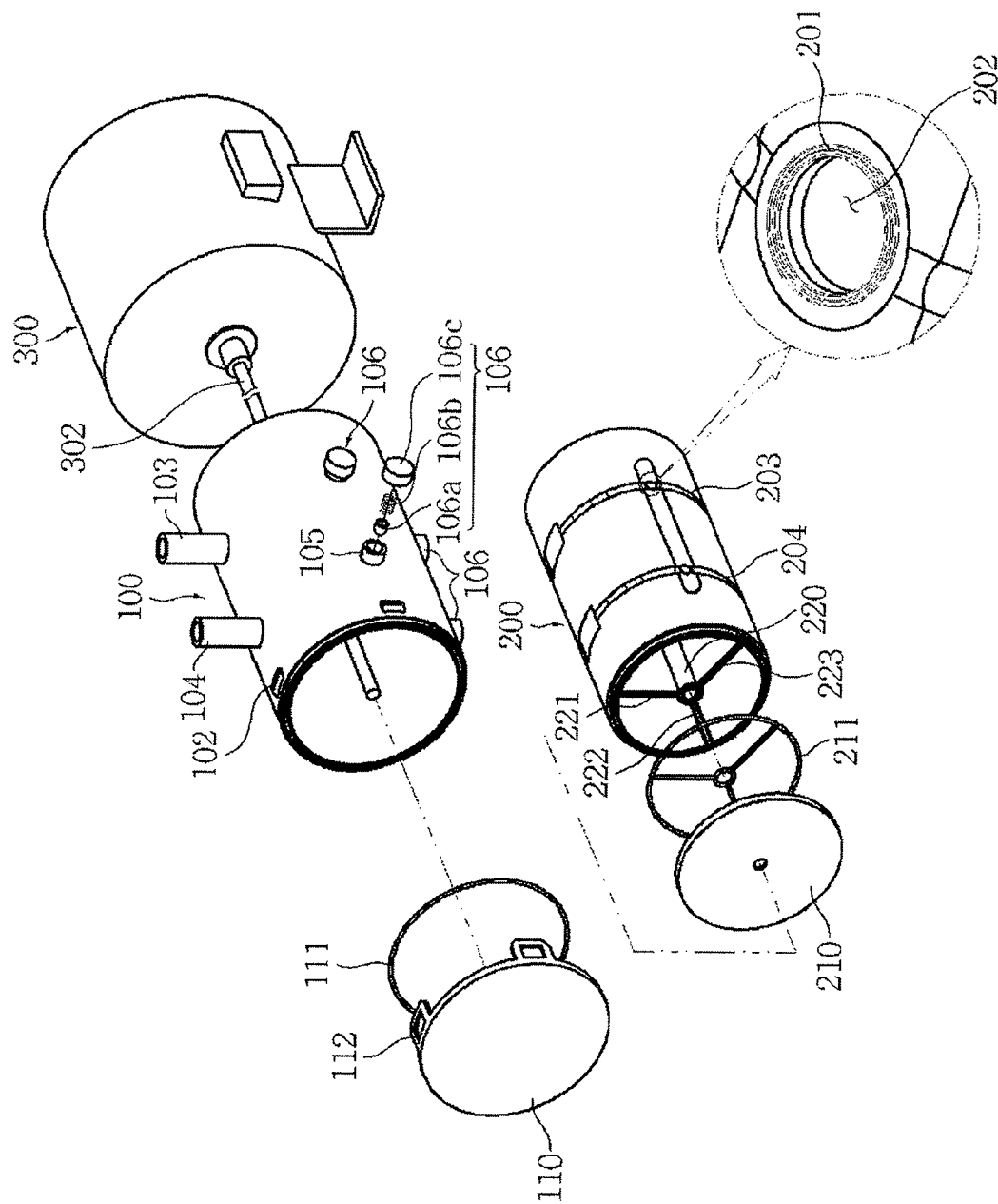
FIG. 17 is an exploded perspective view illustrating an air freshener generating apparatus according to the third embodiment of the present invention.
Figure 18:
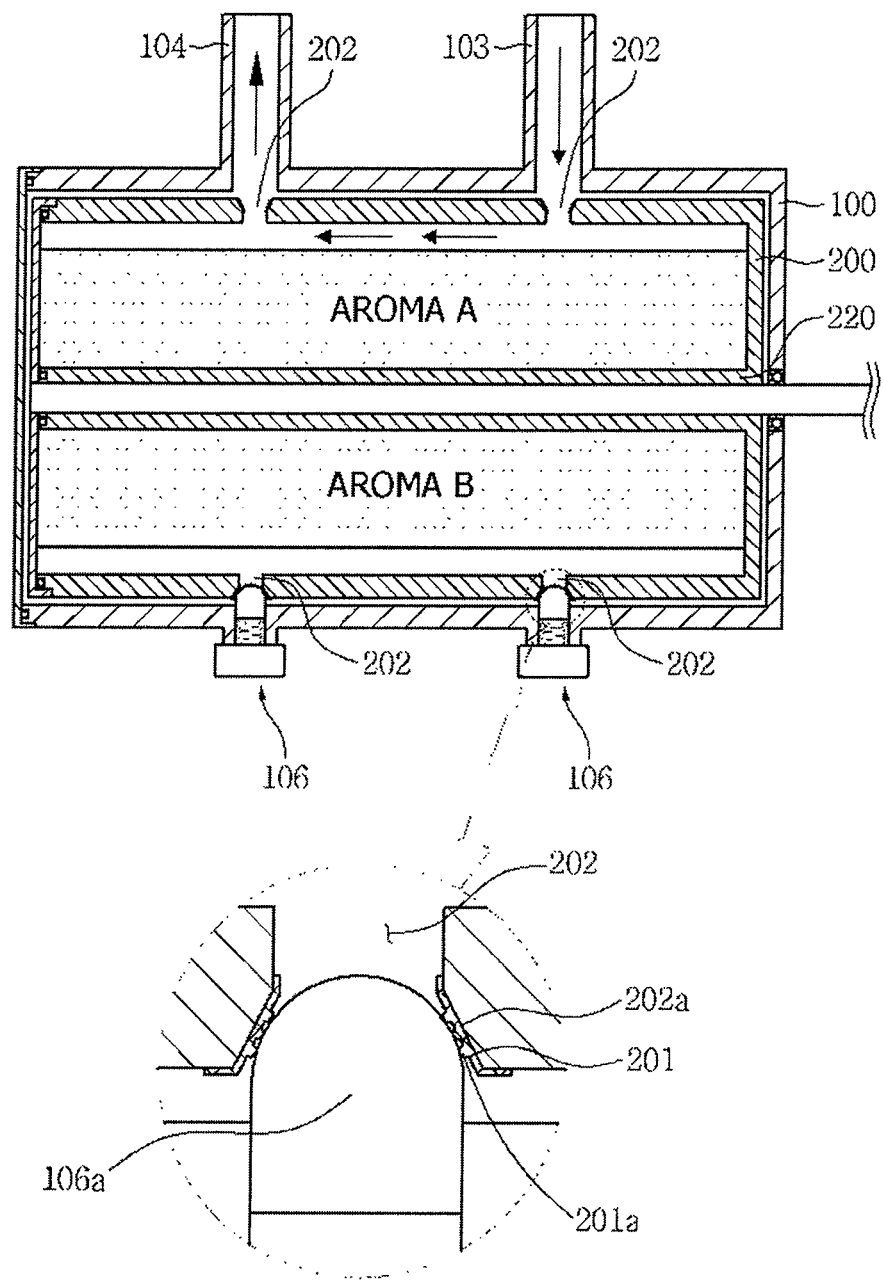
FIG. 18 is a transverse sectional view illustrating the air freshener generating apparatus according to the third embodiment of the present invention.
Figure 19:
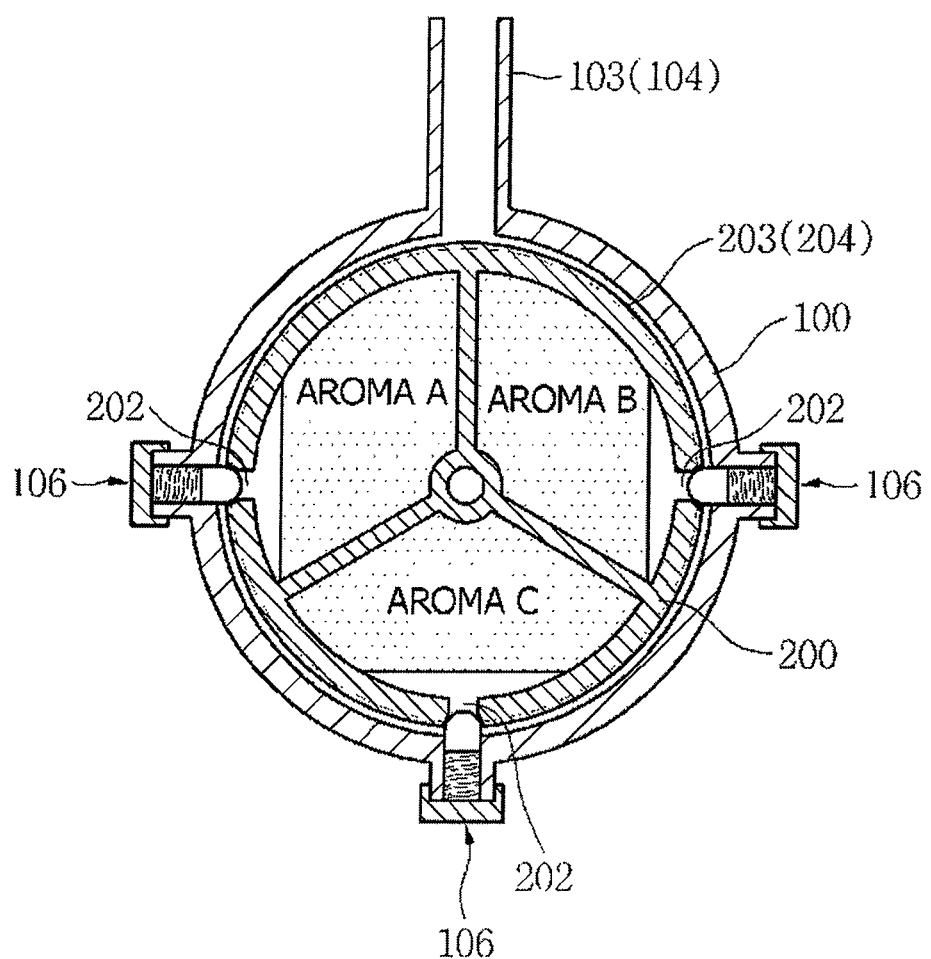
FIG. 19 is a longitudinal sectional view illustrating the air freshener generating apparatus according to the third embodiment of the present invention.

FIG. 17 is an exploded perspective view illustrating an air freshener generating apparatus according to the third embodiment of the present invention. FIG. 18 is a transverse sectional view illustrating the air freshener generating apparatus according to the third embodiment of the present invention. FIG. 19 is a longitudinal sectional view illustrating the air freshener generating apparatus according to the third embodiment of the present invention;

As illustrated in FIG. 17, the air freshener discharging apparatus according to the third embodiment of the present invention includes a body 100, a cartridge 200 mounted within the body 100, and an actuator 300 configured to drive the cartridge 200. Here, the cartridge 200 is mounted on an inner circumferential surface of the body 100.

The body 100 has a cylindrical shape and a cap 110 is coupled with the body 100. Here, a sealing O-ring 111 is interposed between the body 100 and the cap 110. A plurality of coupling portions 112 extend from a tip end of the cap 110 to be coupled to coupling bosses 102 formed at a tip end of the body 100.

An inlet pipe 103 and an outlet pipe 104 radially protrude from a circumferential surface of the body 100 such that they are spaced apart from each other along a lengthwise direction of the body 100 and are communicated with each other.

A plurality of through-holes 105 are formed on the circumferential surface of the body 100 such that they are spaced apart from the inlet pipe 103 and the outlet pipe 104 at certain angles, and ball plungers 106 are mounted on the through-holes 105 respectively. Here, the ball plungers 106 have the same configuration as those of the first embodiment of the present invention, and a detailed description thereof will be omitted.

As illustrated in FIGS. 17 and 18, support members 106a of the ball plungers 106 are coupled to the through-holes 105 such that the balls 106a apply resilient forces toward the center of the cartridge 200 on the outer surface of the cartridge 200.

The cartridge 200 has a cylindrical shape and is mounted within the body 100. A cap 210 is coupled with the cartridge 200. A sealing O-ring 211 is interposed between the cartridge 200 and the cap 210.

A boss 220 is formed at a central portion of the cartridge 200, and three partition walls 221, 222, and 223 are formed with respect to the boss 220 such that different air freshener emitters (an air freshener A emitter, an air freshener B emitter, and an air freshener C emitter) can be filled in the cartridge 200. The cartridge 200 has through-holes 202 at portions facing the ball plungers 106, and grooves 203 and 204 by which the ball plungers 106 are guided are formed on the outer circumferential surface of the cartridge 200.

As illustrated in FIG. 18, an inclined surface 202a inclined at a certain angle is formed at an upper portion of each through-hole 202. Here, the inclined surfaces 202a of the through-holes 202 are formed to come into surface-contact with the ball plungers 106.

A flexible contact member 201 is formed at inner and peripheral portions of each through-hole 202. That is, the flexible contact member 201 made of rubber or silicon is formed along the inclined surface 202a and tip end of the through-hole 202. Here, the flexible contact member 201 serves to widen a contact surface with the ball plunger 106 while it is contacting the ball plunger 106 to be compressed.

A plurality of wrinkled portions 201a is formed in the flexible contact member 201 on the inclined surface 202a of the through-hole 202 at certain intervals. As illustrated in FIG. 18, the wrinkled portions 201a are configured to contact a surface of the ball 106a. The wrinkled portions are preferably formed to have annular bosses such that all of them contact the surface of the ball 106a.

As illustrated in FIG. 17, a rotary shaft 302 of the actuator 300 is inserted into the boss 220 of the cartridge 200 so that the cartridge 200 can be rotated clockwise or counterclockwise.

Here, the actuator 300 is adapted to rotate the cartridge 200 clockwise or counterclockwise at intervals of 90 degrees.

According to the air freshener generating apparatus according to the third embodiment of the present invention, when the ball plungers 106 are coupled to the through-holes 202 of the cartridge 200, the ball plunger 106 contacts and pushes the flexible contact members 201 formed on the inclined surfaces 202a of the through-holes 202 to prevent the air fresheners blocked by the ball plungers from being leaked. Accordingly, an air freshener selected in the cartridge 200 is prevented from being mixed with another air freshener and discharged.

Embodiment 4

Figure 20:
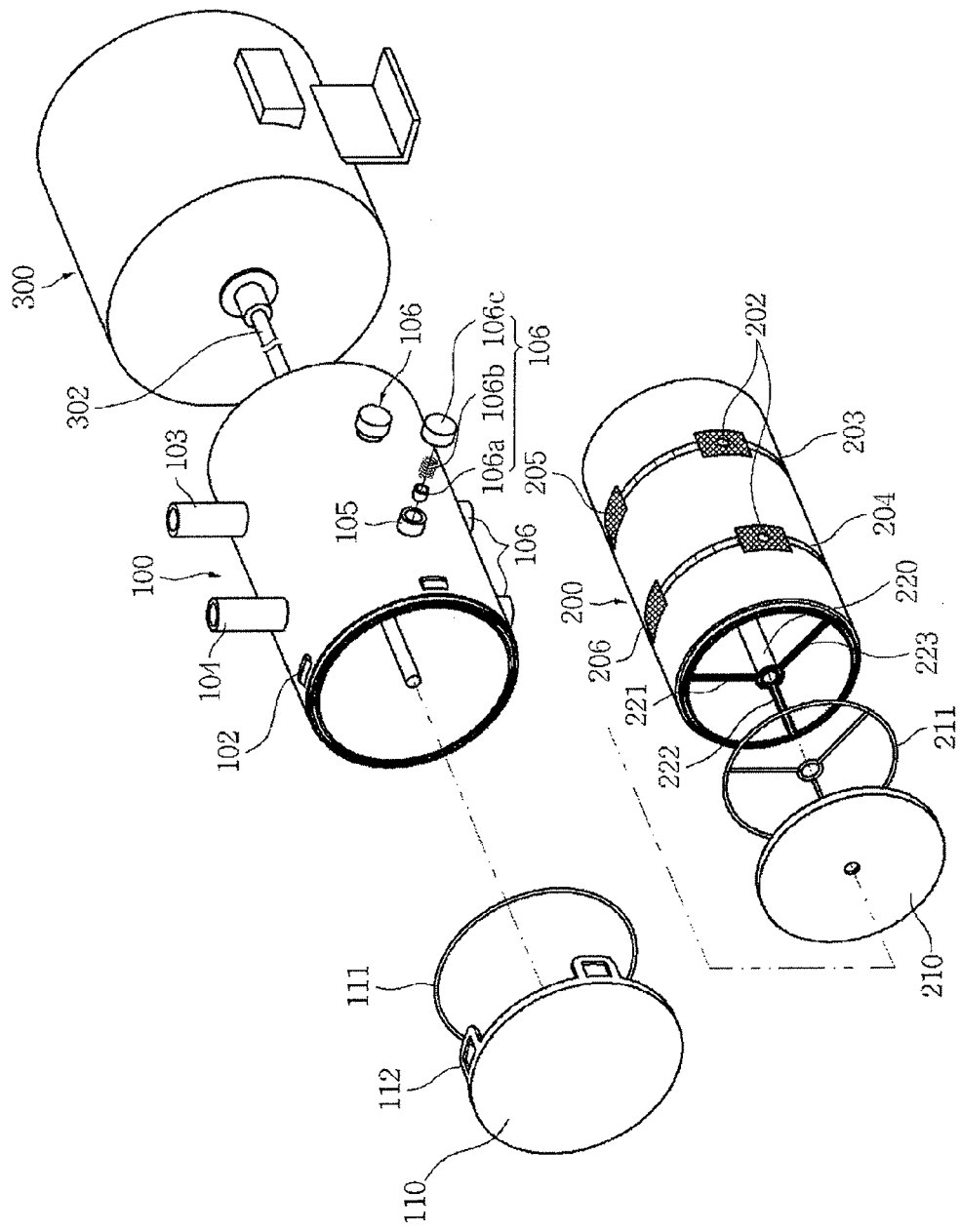
FIG. 20 is an exploded perspective view illustrating an air freshener generating apparatus according to the fourth embodiment of the present invention.
Figure 21:
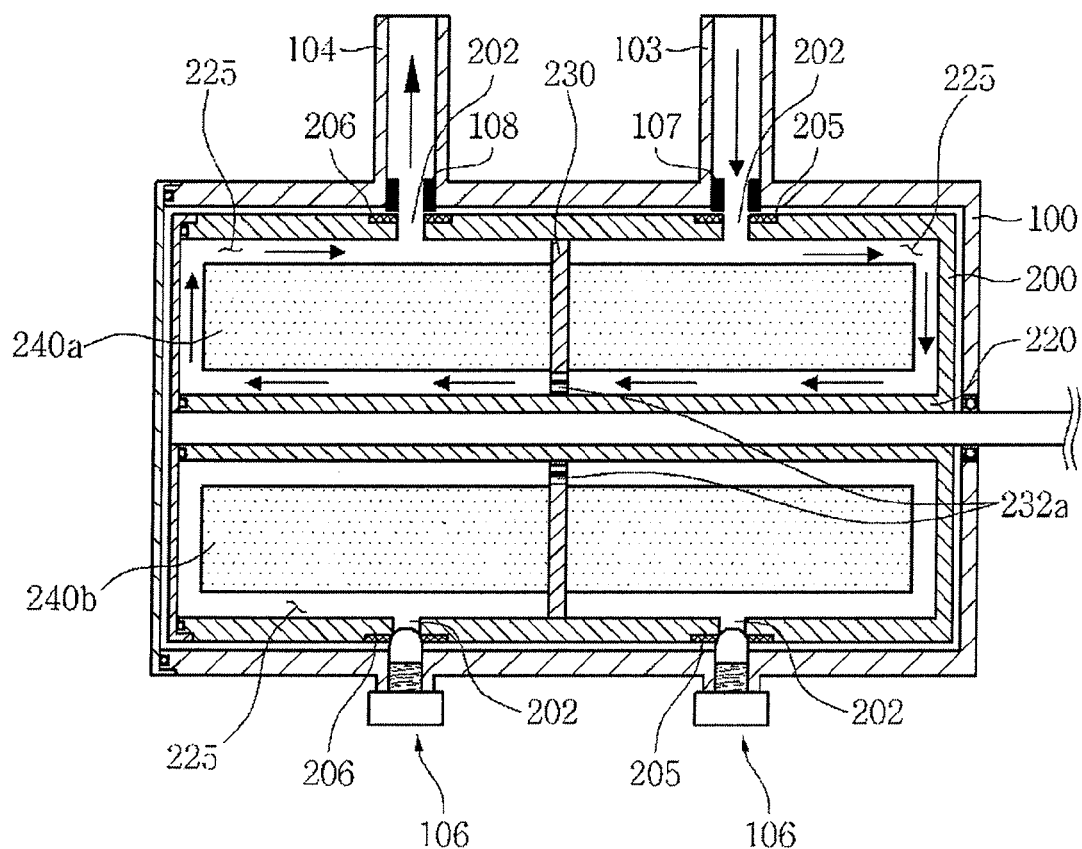
FIG. 21 is a transverse sectional view illustrating the air freshener generating apparatus according to the fourth embodiment of the present invention.
Figure 22:
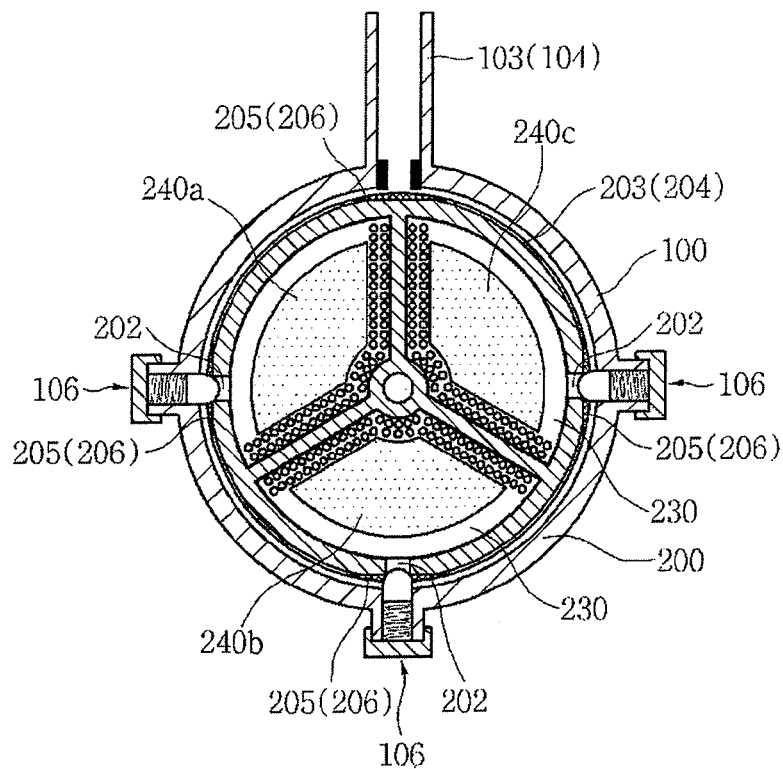
FIG. 22 is a longitudinal sectional view illustrating the air freshener generating apparatus according to the fourth embodiment of the present invention.

FIG. 20 is an exploded perspective view illustrating an air freshener generating apparatus according to the fourth embodiment of the present invention. FIG. 21 is a transverse sectional view illustrating the air freshener generating apparatus according to the fourth embodiment of the present invention. FIG. 22 is a longitudinal sectional view illustrating the air freshener generating apparatus according to the fourth embodiment of the present invention.

As illustrated in FIG. 20, the air freshener generating apparatus according to the fourth embodiment of the present invention includes a body 100, a cartridge 200 mounted within the body 100, and an actuator 300 configured to drive the cartridge 200. Here, the cartridge 200 is mounted on an inner circumferential surface of the body 100. A baffle 230 for supporting air freshener emitters is provided within the cartridge 200.

The body 100 has a cylindrical shape and a cap 110 is coupled with the body 100. Here, a sealing O-ring 111 is interposed between the body 100 and the cap 110. A plurality of coupling portions 112 extend from a tip end of the cap 110 to be coupled to coupling bosses 102 formed at a tip end of the body 100. An inlet pipe 103 and an outlet pipe 104 radially protrude from a circumferential surface of the body 100 such that they are spaced apart from each other along a lengthwise direction of the body 100 and are communicated with each other.

A plurality of through-holes 105 are formed on the circumferential surface of the body 100 such that they are spaced apart from the inlet pipe 103 and the outlet pipe 104 at certain angles, and ball plungers 106 are mounted on the through-holes 105 respectively. Here, the ball plungers 106 have the same configuration as those of the first embodiment of the present invention, and a detailed description thereof will be omitted.

Meanwhile, magnets 107 and 108 are mounted on portions of the body 100 where a communication with the inlet pipe 103 and with the outlet pipe 104 are accomplished.

The cartridge 200 has a cylindrical shape and is mounted within the body 100, and a cap 210 is coupled with the cartridge 200. A sealing O-ring 211 is interposed between the cartridge 200 and the cap 210. A boss 220 is formed at a central portion of the cartridge 200, and three partition walls 221, 222, and 223 are formed with respect to the boss 220 such that different air freshener emitters can be filled in the cartridge 200.

The cartridge 200 has through-holes 202 at portions facing the ball plungers 106, and grooves 203 and 204 by which the ball plungers 106 are guided are formed on the outer circumferential surface of the cartridge 200. Here, the groove 203 is formed along the same circumferential line as the inlet pipe 103, and the groove 204 is formed along the same circumferential line as the outlet pipe 104.

Metal members 205 and 206 are mounted around the through-holes 202 respectively. The magnets 107 and 108 and the metal members 205 and 206 constitute a positioning unit for accurately determining an angular position of the cartridge 200 with respect to the body 100.

As illustrated in FIG. 21, a rotary shaft 302 of the actuator 300 is inserted into the boss 220 of the cartridge 200 so that the cartridge 200 can be rotated clockwise or counterclockwise. The actuator 300 is adapted to rotate the cartridge 200 clockwise or counterclockwise at intervals of 90 degrees.

Figure 23:
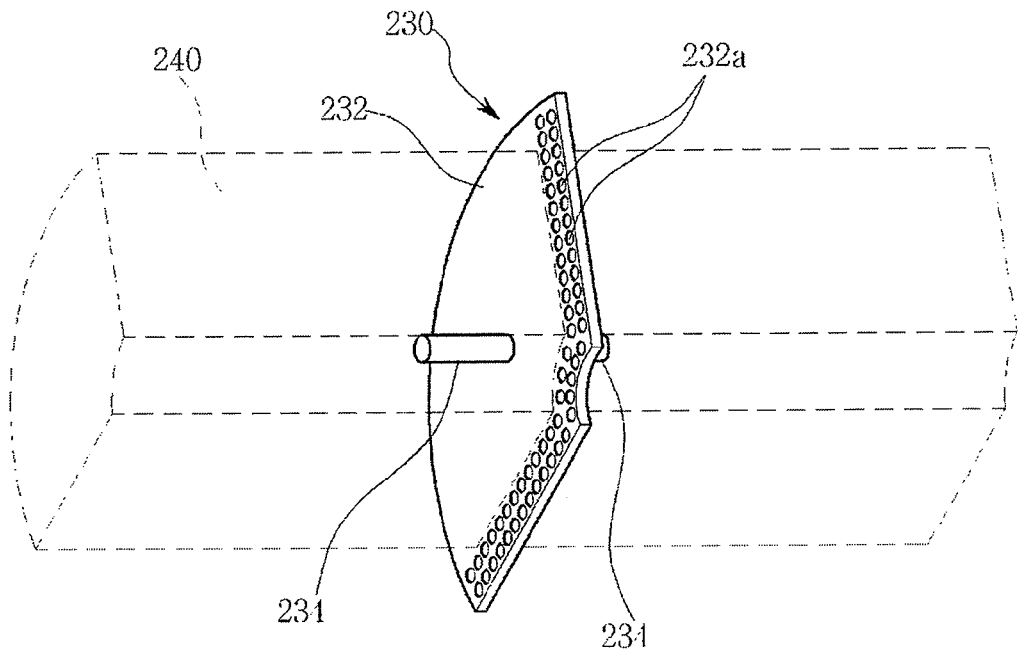
FIG. 23 is a perspective view illustrating a baffle of the air freshener generating apparatus according to the fourth embodiment of the present invention.

As illustrated in FIGS. 21 to 23, the baffle 230 is adapted to support air freshener emitters 240, 240a, 240b, and 240c while blocking passages formed by of partition walls 221, 222, and 223 of the cartridge 200. The baffle 230 includes a plate 232 having a plurality of through-holes 232a within a certain width along a lower circumference thereof, and a support 234 extending to opposite sides from the plate 232 to support the air freshener emitters 240.

Meanwhile, as illustrated in FIG. 21, flow passages 225 through which air flows are formed between the air freshener emitters 240a, 240b, and 240c supported by the baffle 230 and the partition walls 221, 222, and 223.

The through-hole 232a serves as a passage through which air flows from the right side of the plate 232 to left side of the plate 232 in FIG. 21.

The air freshener emitters 240, 240a, 240b, and 240c are preferably made of a solid type and are supported by the supports 234 of the plate 232. It is apparent that liquid type air freshener emitters may be accommodated by modifying the supports 234 of the baffle 230.

Hereafter, an air freshener discharging operation of the air freshener generating apparatus according to the fourth embodiment of the present invention will be described with reference to FIGS. 21, 22, and 24 to 26.

As illustrated in FIG. 22, when a portion of the cartridge 200 where there is no through-hole 202 is located at the inlet pipe 103 of the body 100, air is prevented from being introduced into the cartridge 200. Then, since the ball plungers 106 block all the through-holes 202, respectively, the air fresheners from the emitters 240a, 240b, and 240c are prevented from being discharged.

Figure 24:
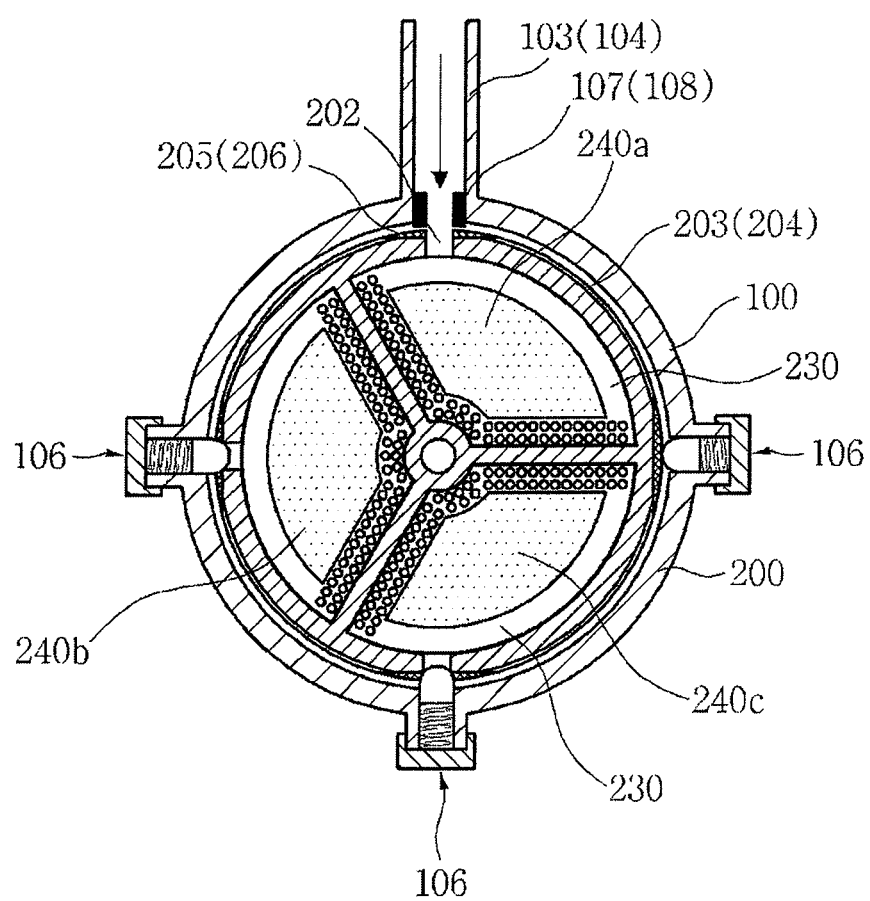
FIGS. 24 to 26 are views illustrating an operation of discharging air fresheners in the air freshener generating apparatus according to the second embodiment of the present invention.

If the cartridge 200 is rotated clockwise by 90 degrees from the state of FIG. 22, air is introduced into the through-hole 202 through the inlet pipe 103 and the air freshener of the emitter 240a is discharged through the outlet pipe 104 as illustrated in FIGS. 21 and 24. Then, as air contacts a surface of the emitter 240a supported by the baffle 230 along the flow passage 225, a sufficient amount of the air freshener is discharged through the outlet pipe 104 together with the air.

Figure 25:
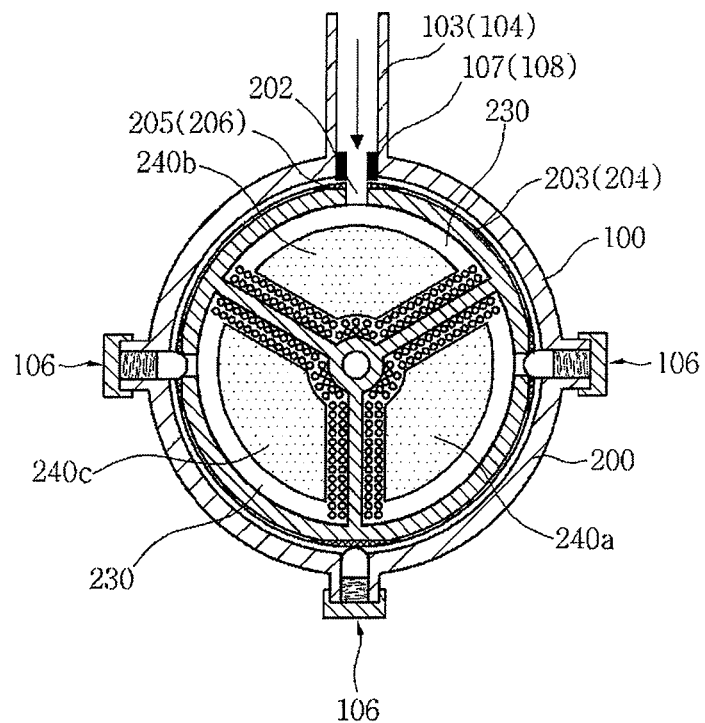

Thereafter, if the cartridge 200 is rotated clockwise by 90 degrees in FIG. 24, air is introduced into the through-hole 202 through the inlet pipe 103 and the air freshener of the emitter 240b is discharged through the outlet pipe 104 as illustrated in FIG. 25.

Figure 26:
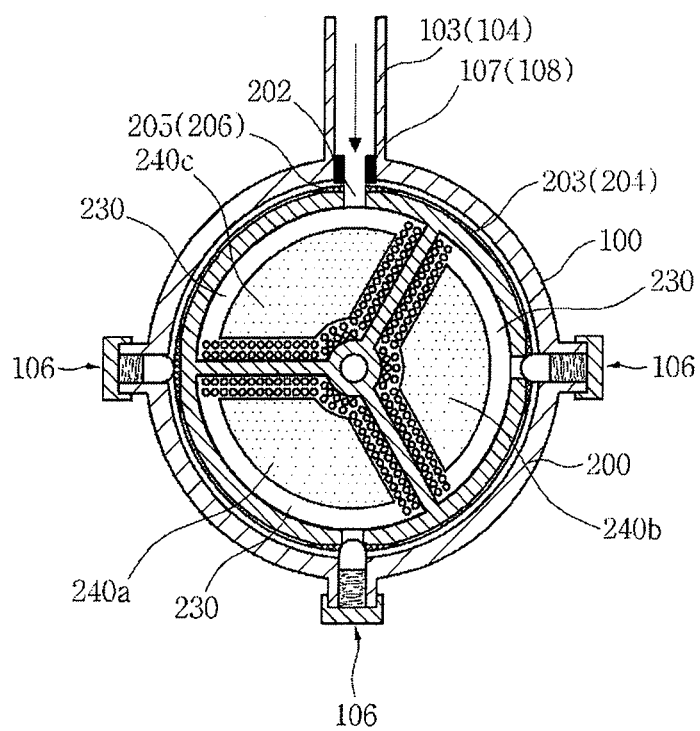

Thereafter, if the cartridge 200 is rotated clockwise by 90 degrees in FIG. 25, air is introduced into the through-hole 202 through the inlet pipe 103 and the air freshener of the emitter 240c is discharged through the outlet pipe 104 as illustrated in FIG. 26.

Meanwhile, if the cartridge 200 is rotated clockwise by 90 degrees in FIG. 26, it returns to the original state of FIG. 22 and air is prevented from being introduced into the cartridge 200, preventing the air freshener of the air freshener emitters 240a, 240b, and 240c from being discharged.

According to the air freshener generating apparatus according to the fourth embodiment of the present invention, since the baffle 230 configured to support the air freshener emitters 240a, 240b, and 240c is mounted on the partition walls 221, 222, and 223 of the cartridge 200 respectively to form the flow passages 225 along the partition walls 221, 222, and 223, the air flowing through the flow passages 225 contacts surfaces of the air freshener emitters 240a, 240b, and 240c, making it possible to sufficiently discharge the air freshener of the air freshener emitters 240a, 240b, and 240c.

Embodiment 5

Figure 27:
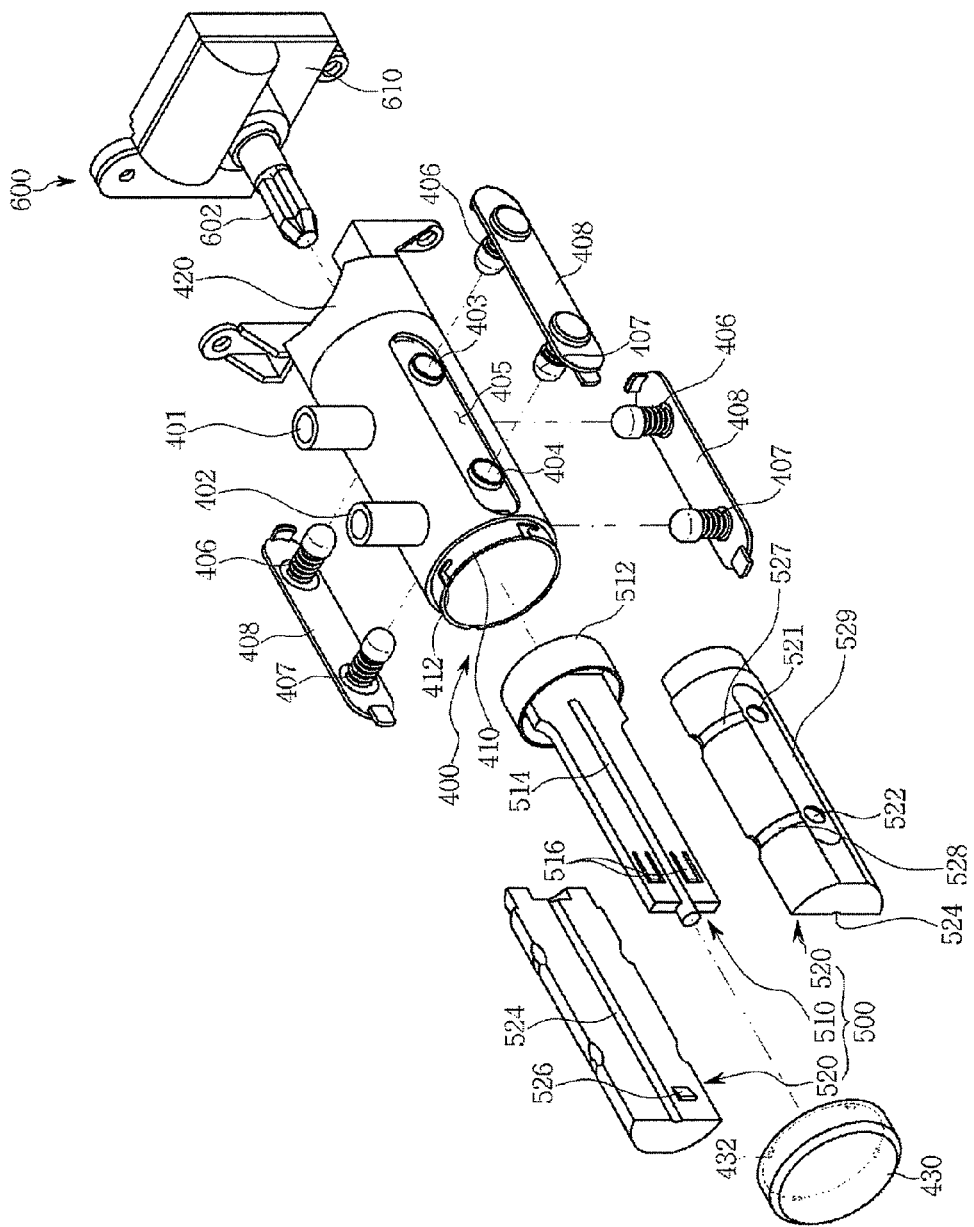
FIG. 27 is an exploded perspective view illustrating an air freshener generating apparatus according to the fifth embodiment of the present invention.
Figure 28:
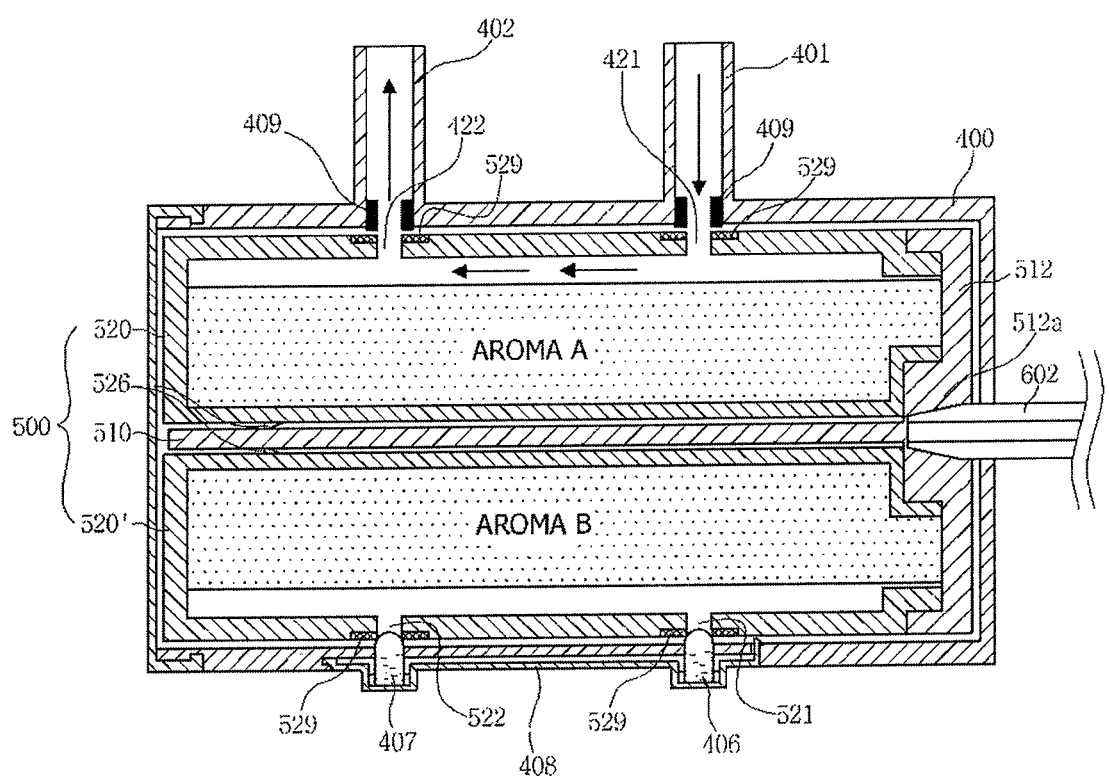
FIG. 28 is a transverse sectional view illustrating the air freshener generating apparatus according to the fifth embodiment of the present invention.

FIG. 27 is an exploded perspective view illustrating an air freshener generating apparatus according to the fifth embodiment of the present invention. FIG. 28 is a transverse sectional view illustrating the air freshener generating apparatus according to the fifth embodiment of the present invention.

As illustrated in FIGS. 27 and 28, the air freshener generating apparatus for a vehicle according to the fifth embodiment of the present invention includes a body 400, a cartridge 500 mounted within the body 400 and having a holding plate 510 and sub-cartridges 520 and 520', and an actuator 600 configured to drive the cartridge 500. Here, the cartridge 500 may be mounted on an inner circumferential surface of the body 400.

As illustrated in FIG. 27, the body 400 has a cylindrical shape and an inlet pipe 401 and an outlet pipe 402 radially protrude from a circumferential surface of the body 400 such that they are spaced apart from each other along a lengthwise direction of the body 400 and are communicated with each other. A plurality of through-holes 403 and 404 are formed on the circumferential surface of the body 400 such that they are spaced apart from the inlet pipe 401 and the outlet pipe 402 at certain angles, and insertion recesses 405 are formed on peripheries of the through-holes 403 and 404 in a lengthwise direction of the circumferential surface of the body 400. Ball plungers 406 and 407 are mounted on the through-holes 403 and 403. The ball plungers 406 and 407 are connected to each other by means of connecting members 408, and the connecting members 408 are inserted into the insertion recesses 405.

Here, three sets of ball plungers 406 and 407 are provided along the same circumferential lines as the inlet pipe 103 and the outlet pipe 402 at intervals of 90 degrees, and are mounted on the through-holes 403 and 404, respectively. Here, as illustrated in FIGS. 28 and 29, the ball plungers 406 and 407 are coupled to the through-holes 403 and 404 to apply resilient forces on outer circumferential surface of the cartridge 500 toward the center of the cartridge 500.

Figure 29:
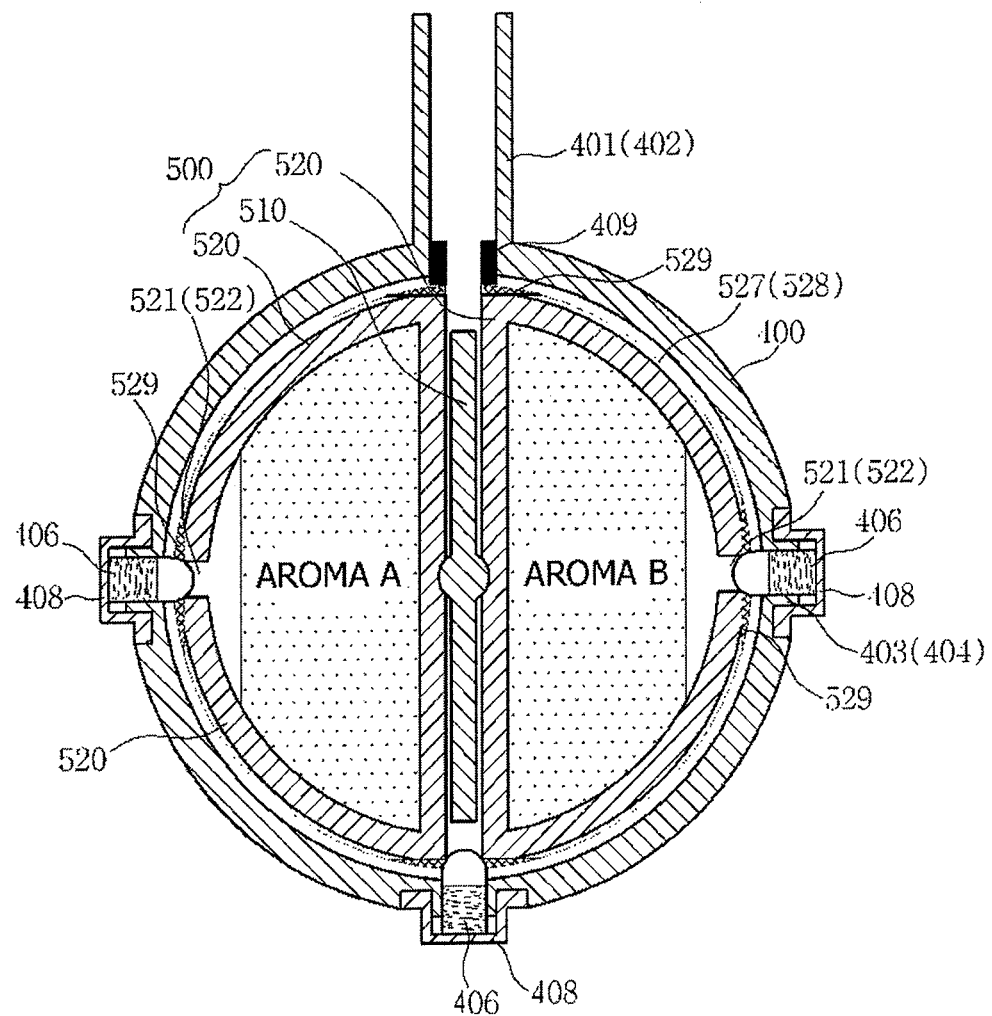
FIG. 29 is a longitudinal sectional view illustrating the air freshener generating apparatus according to the fifth embodiment of the present invention.

As illustrated in FIGS. 28 and 29, magnets 409 are mounted on portions of the body 400 where a communication with the inlet pipe 401 and with the outlet pipe 402 are accomplished.

A stepped portion 410 is formed at one tip end of the body 400, and a support 420 is formed at the other tip end of the body 400 to be coupled to the actuator 600. A cap 430 is coupled to the stepped portion 410 of the body 400. That is, a plurality of coupling grooves 412 are formed on a circumferential surface of the stepped portion 410, and a plurality of coupling bosses 432 coupled to the coupling grooves 412 respectively protrude from an inner surface of the cap 430.

As illustrated in FIG. 27, the cartridge 500 includes a holding plate 510 having a coupling portion 512 at one side thereof, and at least two sub-cartridges 520 and 520' independently coupled to the coupling portion 512 of the holding plate 510 and having through-holes 521 and 522 at locations facing the ball plungers 406 and 407, respectively. Different air freshener emitters (an air freshener A emitter and an air freshener B emitter) are filled in the sub-cartridges 520 and 520'.

A coupling portion 512 into which tip ends of the sub-cartridges 520 and 520' are inserted is formed at one tip end of the holding plate 510. A guide rod 514 is formed along the center line of the holding plate 510 and cutaway portions 516 are formed on upper and lower sides of the guide rod 514. A coupling recess 512a is formed in the coupling portion 512 to be coupled to the coupling shaft 602 of the actuator 600. Here, the holding plate 510 is coupled to the sub-cartridges 520 and 520' to serve as a rotating body for rotating the cartridge 500.

The sub-cartridges 520 and 520' have through-holes 521 and 522 at locations facing the ball plungers 406 and 407, and each sub-cartridge has a guide recess 524 and a boss 526 corresponding to the guide rod 514 and the cutaway portion 516. Here, the boss 526 has a wedge-like shape.

Grooves 527 and 528 by which the ball plungers 406 and 407 are guided are formed in the sub-cartridges 520 and 520' along circumferential lines of the sub-cartridges 520 and 520'.

The guide rod 514 of the holding plate 10 is coupled to the guide recesses 524 and the bosses 526 are coupled to the cutaway portions 516 of the holding plate 510, respectively.

Metal members 529 are mounted on the sub-cartridges 520 and 520' around the through-holes 521 and 522. Here, the metal members 529 constitute a positioning unit for positioning the cartridge 500 at an accurate angle with respect to the body 400 together with the magnets 409.

As illustrated in FIG. 27, the coupling shaft 602 of the actuator 600 is inserted into the coupling recess 512a formed at the coupling portion 512 of the cartridge 500 so that the cartridge 500 can be rotated clockwise or counterclockwise. A support plate 610 is formed in the actuator 600 to be coupled to the support 420 of the body 400. Here, the actuator 600 is configured to rotate the cartridge 500 clockwise or counterclockwise at a certain angle.

Meanwhile, although two sub-cartridges 520 and 520' are coupled to the holding plate 510 in the fifth embodiment, three sub-cartridges may be installed in the holding plate 510.

Hereinafter, a process of discharging air fresheners in the air freshener generating apparatus according to the present invention will be described with reference to FIGS. 28 to 32.

As illustrated in FIG. 29, if the holding plate 510 of the cartridge 500 is located to face the inlet pipe 401 of the body 400, air is prevented from being introduced into the sub-cartridges 520 and 520'. Then, all the ball plungers 406 and 407 block the through-holes 521 and 522 of the sub-cartridges 520 and 520', thereby preventing air fresheners (the air freshener A and the air freshener B) from being discharged.

If the cartridge 500 is rotated clockwise by 90 degrees in FIG. 29, air is introduced through the through-hole 521 via the inlet pipe 401 and then the air freshener A is discharged through the outlet pipe 402. Here, when the cartridge 500 is rotated clockwise, the ball plungers 406 are guided by the grooves 527 and 528, and when the ball plungers 406 approach the inlet pipe 401 and the outlet pipe 402, the through-holes 221 and 222 face the inlet pipe 401 and the outlet pipe 402 by the positioning unit, i.e., the magnets 409 and the metal members 529.

Figure 30:
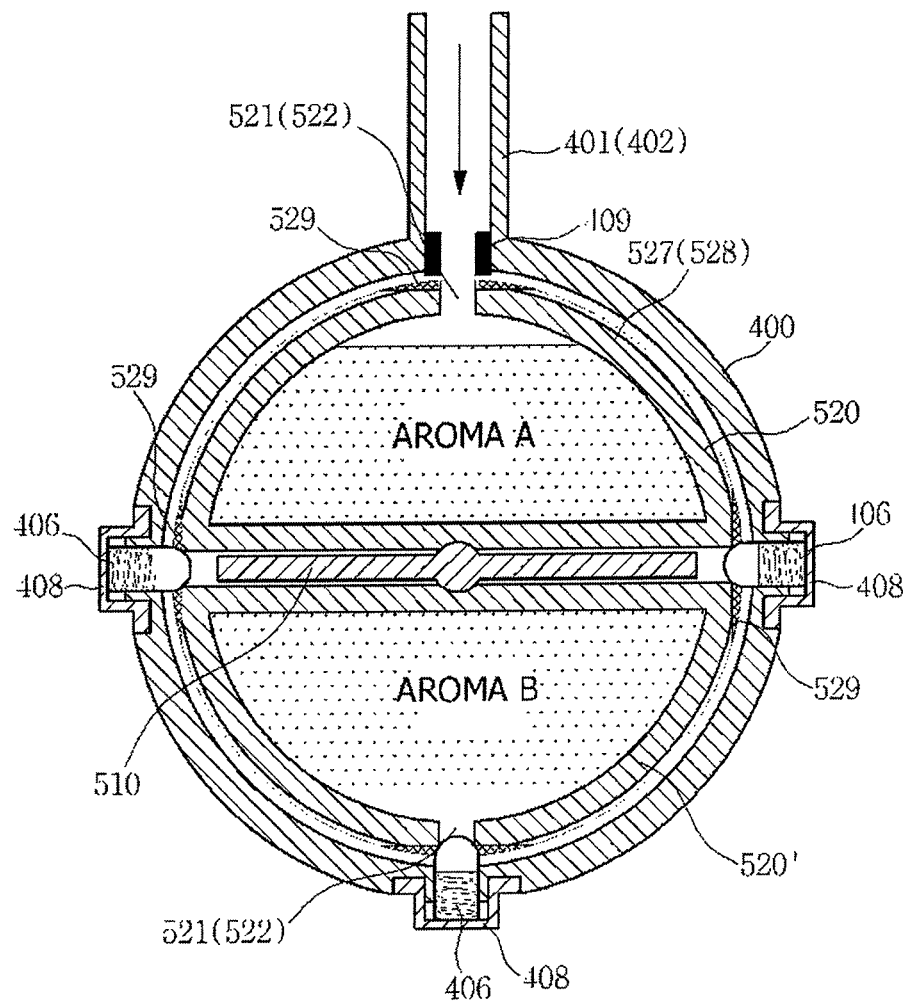
FIGS. 30 to 32 are views illustrating an operation of discharging air fresheners in the air freshener generating apparatus according to the fifth embodiment of the present invention.

Thereafter, if the cartridge 200 is rotated clockwise by 90 degrees in FIG. 30, the holding plate 510 of the cartridge 500 faces the inlet pipe 401 of the body 400. Then, the ball plungers 406 and 407 block the through-holes 521 and 522, thereby preventing the air fresheners (the air freshener A and the air freshener B) from being discharged. Here, FIG. 31 illustrates a state where the cartridge 200 is rotated 180 degrees from the state of FIG. 29.

Figure 31:
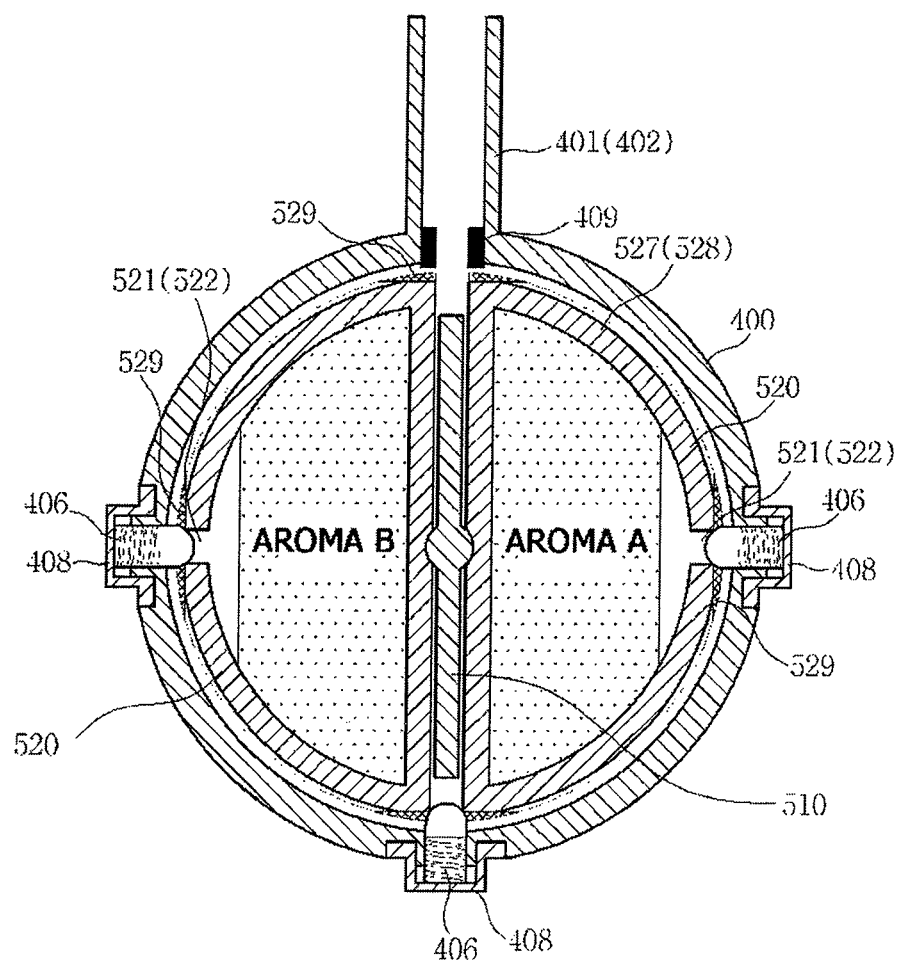
Figure 32:
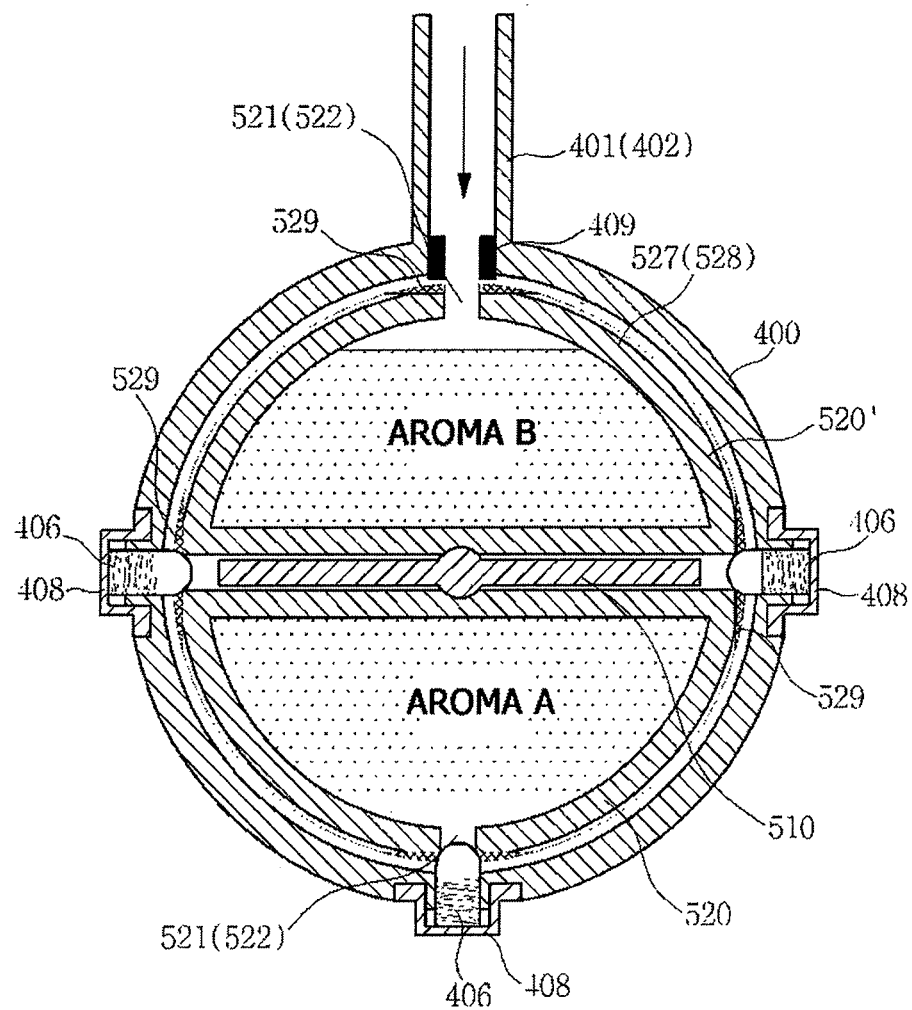

Thereafter, if the cartridge 500 is rotated clockwise by 90 degrees in FIG. 31, air is introduced into the through-hole 521 via the inlet pipe 401, allowing the air freshener B to be withdrawn through the outlet pipe 402.

Meanwhile, if the cartridge 500 is sequentially rotated counterclockwise 90 degrees from the position of FIG. 29, the air freshener B is discharged, the air fresheners are not discharged, and the air freshener A is discharged.

Meanwhile, when an air freshener emitter is filled in one of the sub-cartridges 520 and 520', only an ON/OFF function is necessary. Therefore, rotational angle could be in a range of 10 to 350 degrees. Accordingly, a rotation angle can be minimized, which reduces the durability and power consumption of the air freshener generating apparatus.

According to the air freshener generating apparatus for a vehicle of the fifth embodiment of the present invention, the cartridge 500 mounted within the body 400 is divided, allowing a user to easily change a desired air freshener.

INDUSTRIAL APPLICABILITY

According to an air freshener generating apparatus for a vehicle air conditioning system of the present invention, its structure can be simplified as compared with a conventional air freshener generating apparatus and a cartridge can be easily exchanged.

The invention claimed is:

1. An air freshener generating apparatus of a vehicle air conditioning system, the air freshener generating apparatus comprising:
a body in which an inlet pipe is communicated with an outlet pipe and on a circumferential surface of which ball plungers are mounted at intervals along circumferential lines on which the inlet pipe and the outlet pipe are located respectively;
a cartridge rotatably coupled to the body and having at least one partition wall such that at least one air freshener emitter is filled within spaces defined by the partition wall, the cartridge having through-holes facing the ball plungers; and
an actuator configured to rotate the cartridge by a predetermined angle,
wherein, when the cartridge is rotated by the predetermined angle, air is supplied through the through-hole facing the inlet pipe such that one air freshener is discharged through the through-hole facing the outlet pipe, and the ball plungers are configured to block the rest of the through-holes.

2. The air freshener generating apparatus as claimed in claim 1, wherein the cartridge is mounted on inner circumferential surface of the body and resilient force of the ball plunger is applied on outer circumferential surface of the cartridge toward the center of the cartridge.

3. The air freshener generating apparatus as claimed in claim 1, wherein the cartridge is mounted on outer circumferential surface of the body and resilient force of the ball plunger is applied on inner circumferential surface of the cartridge.

4. The air freshener generating apparatus as claimed in claim 1, further comprising a positioning unit including magnets mounted on portions of the body where a communication with the inlet pipe and with the outlet pipe are accomplished, and metal members mounted on peripheries of the through-holes of the cartridge.

5. The air freshener generating apparatus as claimed in claim 2, wherein grooves by which the ball plungers are guided are formed in a plurality of rows on the outer circumferential surface of the cartridge.

6. The air freshener generating apparatus as claimed in claim 3, wherein grooves by which the ball plungers are guided are formed in a plurality of rows on the inner circumferential surface of the cartridge.

7. The air freshener generating apparatus as claimed in claim 2, wherein, whenever the cartridge is rotated clockwise or counterclockwise by 90 degrees with respect to the body, different air fresheners are selected and discharged.

8. The air freshener generating apparatus as claimed in claim 1, wherein the cartridge has flexible contact members on inner and peripheral portions of the through-holes so that the ball plungers contact and push the flexible contact members to prevent air fresheners from being leaked.

9. The air freshener generating apparatus as claimed in claim 8, wherein inclined surfaces having a certain angle are formed at upper portions of the through-holes so that the ball plungers come into surface-contact with the flexible contact members.

10. The air freshener generating apparatus as claimed in claim 9, wherein a plurality of wrinkled portions are formed in the flexible contact members on the inclined surface at certain intervals.

11. The air freshener generating apparatus as claimed in claim 1, wherein baffles configured to block a passage formed by the partition wall and to let the air fresheners pass through lower portion thereof are mounted on the cartridge, the air freshener emitters being supported by the baffle, and flow passages being formed along a periphery of the partition wall.

12. The air freshener generating apparatus as claimed in claim 11, wherein the baffle includes a plate having a plurality of through-holes within a certain width at a lower circumference thereof and a support extending to opposite sides from the plate to support the air freshener emitter.

13. An air freshener generating apparatus for a vehicle, air freshener generating apparatus comprising:
   a body in which an inlet pipe and an outlet pipe are formed to be communicated with each other and on which ball plungers are mounted along a circumferential surface thereof at a predetermined interval;
   a cartridge mounted within the body and filled with at least one air freshener emitter; and
   an actuator configured to rotate the cartridge by a predetermined angle,
   wherein the cartridge includes a holding plate having a coupling portion at one side thereof, and at least one sub-cartridges independently coupled to the coupling portion of the holding plate and having through-holes respectively,
   wherein a guide rod is formed along a center line of the holding plate and cutaway portions are formed on upper and lower sides of the guide rod, each sub-cartridge has a guide recess and a boss corresponding to the guide rod and the cutaway portion, and the guide rod is coupled to the guide recesses and the bosses are coupled to the cutaway portions, respectfully,
   and
   wherein, when the cartridge is rotated by the predetermined angle, air is supplied through the through-hole facing the inlet pipe such that one air freshener is discharged through the through-hole facing the outlet pipe, and the ball plungers are configured to block the rest of the through-holes.

14. The air freshener generating apparatus as claimed in claim 13, wherein two sub-cartridges are provided and the air freshener emitter is filled in one of the two sub-cartridges.

15. The air freshener generating apparatus as claimed in claim 2, further comprising a positioning unit including magnets mounted on portions of the body where a communication with the inlet pipe and with the outlet pipe are accomplished, and metal members mounted on peripheries of the through-holes of the cartridge.

16. The air freshener generating apparatus as claimed in claim 3, further comprising a positioning unit including magnets mounted on portions of the body where a communication with the inlet pipe and with the outlet pipe are accomplished, and metal members mounted on peripheries of the through-holes of the cartridge.

17. The air freshener generating apparatus as claimed in claim 3, wherein, whenever the cartridge is rotated clockwise or counterclockwise by 90 degrees with respect to the body, different air fresheners are selected and discharged.

\* \* \* \* \*